United States Patent
Mao et al.

(10) Patent No.: US 10,357,190 B1
(45) Date of Patent: Jul. 23, 2019

(54) MEDICAL DEVICE PROBE AND CONNECTOR

(71) Applicant: ViOptix, Inc., Newark, CA (US)

(72) Inventors: Jimmy Jian-min Mao, Fremont, CA (US); Robert E. Lash, Redwood City, CA (US)

(73) Assignee: ViOptix, Inc., Newark, CA (US)

( * ) Notice: Subject to any disclaimer, the term of this patent is extended or adjusted under 35 U.S.C. 154(b) by 81 days.

(21) Appl. No.: 15/445,656

(22) Filed: Feb. 28, 2017

Related U.S. Application Data

(63) Continuation of application No. 14/754,622, filed on Jun. 29, 2015, now Pat. No. 9,579,051, which is a continuation of application No. 13/777,285, filed on Feb. 26, 2013, now Pat. No. 9,066,692, which is a continuation of application No. 12/477,611, filed on Jun. 3, 2009, now Pat. No. 8,382,666.

(51) Int. Cl.
*A61B 5/1455* (2006.01)
*G02B 6/38* (2006.01)

(52) U.S. Cl.
CPC ........ *A61B 5/14552* (2013.01); *G02B 6/3817* (2013.01); *G02B 6/3885* (2013.01); *A61B 2562/227* (2013.01); *A61B 2562/228* (2013.01)

(58) Field of Classification Search
CPC .................................................. A61B 5/14552
USPC ......................................................... 362/574
See application file for complete search history.

(56) References Cited

U.S. PATENT DOCUMENTS

| | | |
|---|---|---|
| 3,394,700 A | 7/1968 | Yamamoto |
| 3,690,769 A | 9/1972 | Mori |
| 3,729,006 A | 4/1973 | Wilder et al. |
| 3,776,240 A | 12/1973 | Woodson |
| 3,855,567 A | 12/1974 | Harms |
| D235,549 S | 6/1975 | Funderburk |
| 4,049,000 A | 9/1977 | Williams |
| 4,190,042 A | 2/1980 | Sinnreich |
| 4,226,228 A | 10/1980 | Shin et al. |
| 4,426,127 A | 1/1984 | Kubota |
| 4,927,374 A | 5/1990 | Batty |
| 4,945,896 A | 8/1990 | Gade |

(Continued)

OTHER PUBLICATIONS

Jameco Electronics Catalog, AMP/Tyco Electronics Interconnect Part No. 206044-1 (Jameco P/N 495031), available at http://www.jameco.com, accessed Jun. 3, 2009 (for exam purposes, use publication date of Jan. 1, 2008).

(Continued)

*Primary Examiner* — Lynnsy M Summitt
*Assistant Examiner* — Tara Rose E Carter
(74) *Attorney, Agent, or Firm* — Aka Chan LLP

(57) ABSTRACT

A sensor probe has a connector and the connector's corresponding receptacle on a console have security mechanisms that ensure that the connector and the receptacle are properly connected and mated. The connector and receptacle can have physical security features that block insertion of the connector into the receptacle if they are not aligned in a proper orientation. The console can also include a software security feature that allows optical measurements from the sensor probe only if the connector of the sensor probe and receptacle on the console are connected properly. An adapter can also be used to convert a conventional receptacle mounted on a console into a receptacle with security features.

28 Claims, 12 Drawing Sheets

(56) References Cited

U.S. PATENT DOCUMENTS

| | | |
|---|---|---|
| 4,954,094 A | 9/1990 | Humphrey |
| 4,959,067 A | 9/1990 | Muller |
| D312,306 S | 11/1990 | Michelson |
| D318,116 S | 7/1991 | Michelson |
| 5,230,621 A | 7/1993 | Jacoby |
| 5,769,781 A | 6/1998 | Chappuis |
| 5,891,018 A | 4/1999 | Wells |
| D442,687 S | 5/2001 | Schulz |
| 6,309,219 B1 | 10/2001 | Robert |
| 6,322,499 B1 | 11/2001 | Evans et al. |
| 6,416,465 B2 | 7/2002 | Brau |
| 6,602,188 B2 | 8/2003 | Bolser |
| D522,140 S | 5/2006 | Stalcup et al. |
| 7,153,279 B2 | 12/2006 | Ayad |
| D535,744 S | 1/2007 | Wright |
| 7,226,413 B2 | 6/2007 | McKinley |
| 7,261,689 B2 | 8/2007 | Holland et al. |
| 7,355,688 B2 | 4/2008 | Lash et al. |
| 7,361,140 B2 | 4/2008 | Ries et al. |
| D575,398 S | 8/2008 | Lash et al. |
| 7,525,647 B2 | 4/2009 | Lash et al. |
| D593,201 S | 5/2009 | Lash et al. |
| 2002/0062070 A1 | 5/2002 | Tschupp et al. |
| 2007/0032738 A1 | 2/2007 | Flaherty et al. |
| 2008/0106792 A1* | 5/2008 | Lash .................. G01N 21/3151 359/618 |
| 2008/0300571 A1* | 12/2008 | LePivert ............ A61B 18/1492 604/503 |
| 2008/0319290 A1 | 12/2008 | Mao et al. |

OTHER PUBLICATIONS

ViOptix Probe Cable Connector Information, 1 page (for exam purposes, use publication date of Jan. 1, 2008).

Delta Surgical Instruments Product Catalog, Jun. 2006, pp. 35-39.

Elevators, Codman Surgical Product Catalog, S-53-S-60, N-162, (2004).

U.S. Appl. No. 12/194,508, filed Aug. 19, 2008, available via IFW (see tile history incl. office action with notification date of Jun. 19, 2012, and office action with notification date of Mar. 7, 2013).

* cited by examiner

Figure 4A
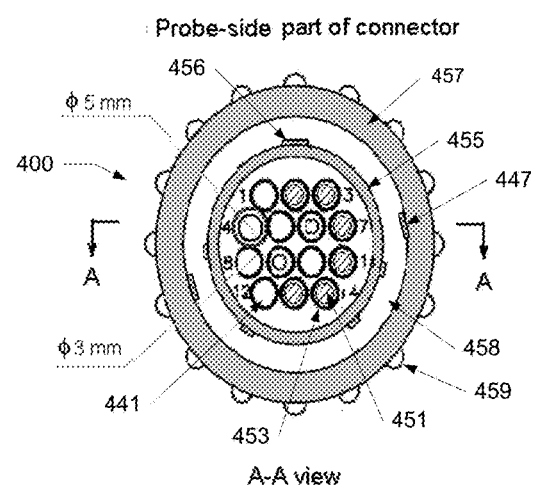
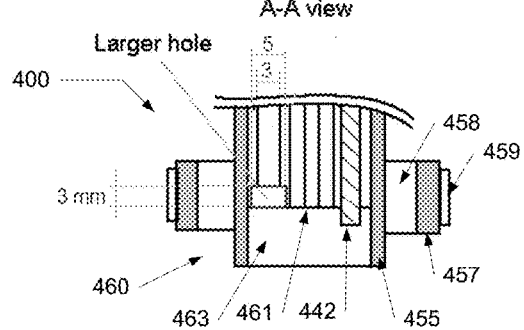
Figure 4B
Figure 5A
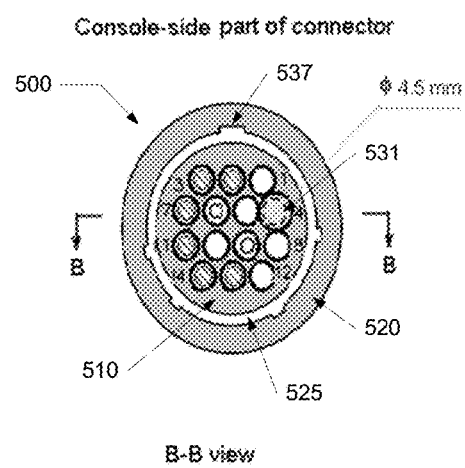
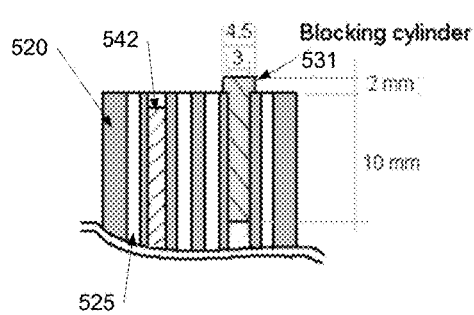
Figure 5B

Figure 6B                    Figure 6C

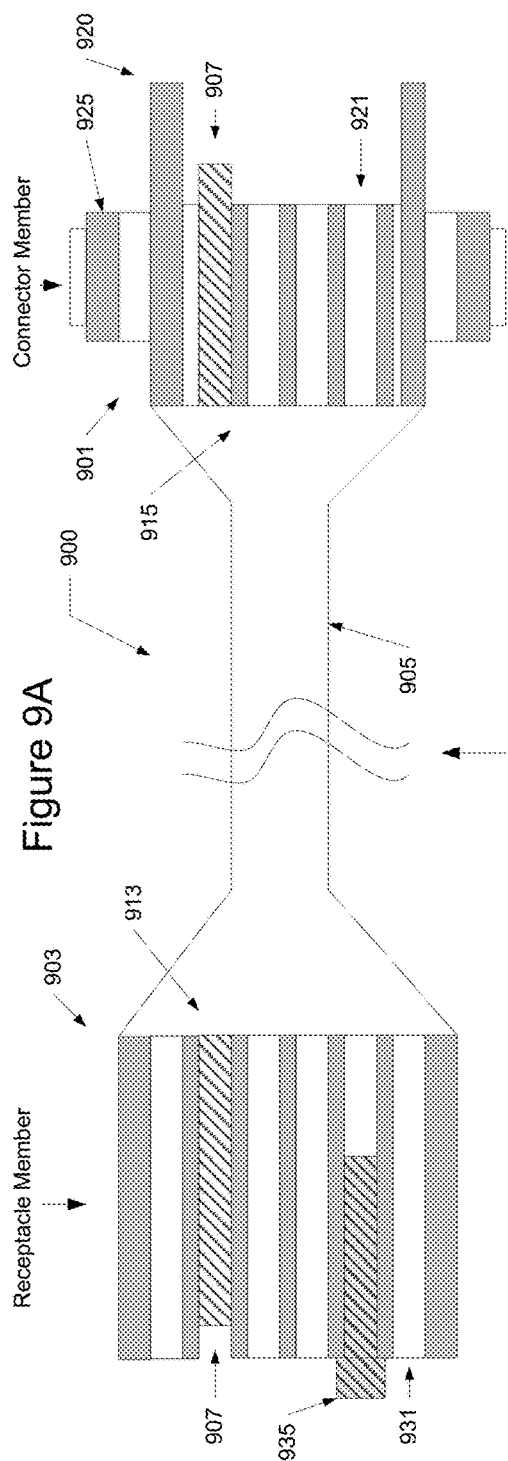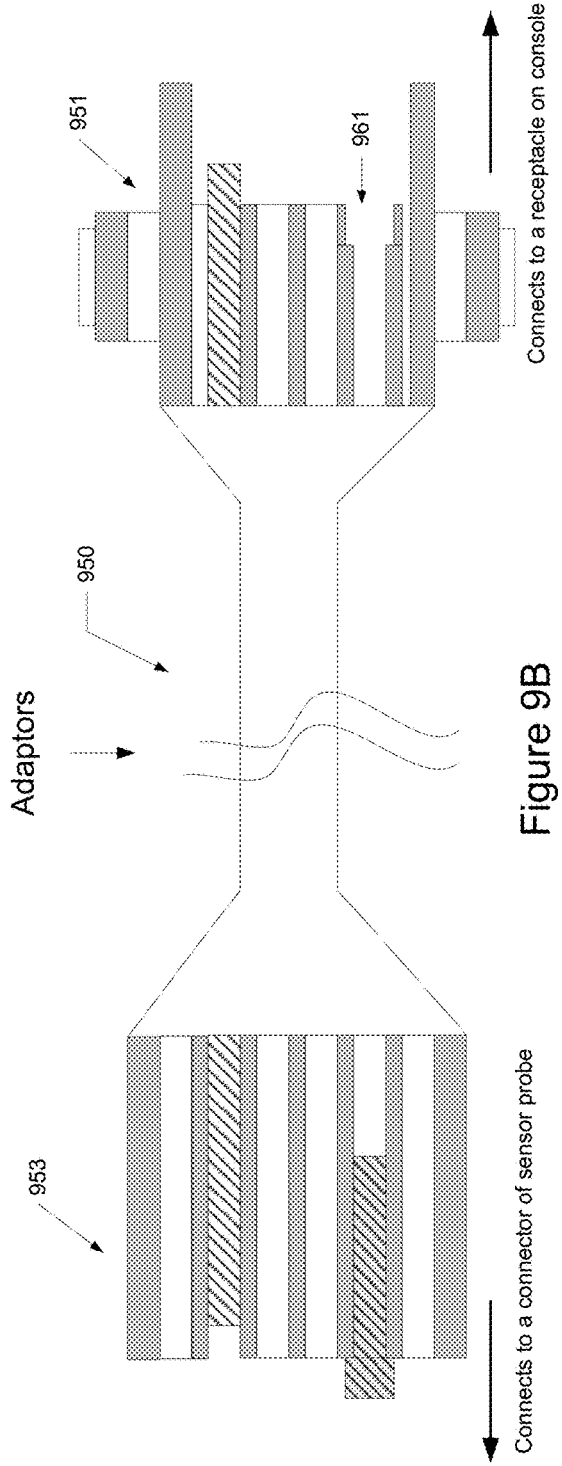
Figure 9A
Figure 9B

MEDICAL DEVICE PROBE AND CONNECTOR

CROSS-REFERENCE TO RELATED APPLICATIONS

This patent application is a continuation of U.S. patent application Ser. No. 14/754,622, filed Jun. 29, 2015, issued as U.S. Pat. No. 9,579,051 on Feb. 28, 2017, which is a continuation of U.S. patent application Ser. No. 13/777,285, filed Feb. 26, 2013, issued as U.S. Pat. No. 9,066,692 on Jun. 30, 2015, which is a continuation of U.S. patent application Ser. No. 12/477,611, filed Jun. 3, 2009, issued as U.S. Pat. No. 8,382,666 on Feb. 26, 2013. These applications are incorporated by reference along with all other references cited in this application.

BACKGROUND OF THE INVENTION

Connectors are an essential part of any device involving optical or electrical communication. Connectors can be used to join lengths of conductors (e.g., optical fibers or electrical wires) into longer lengths, or to provide optical or electrical connection of one device to another. Generally, a connector must axially align a terminal end of an optical fiber or electrical wire with a terminal end of another optical fiber or electrical wire. It is important that there is no or minimal signal transmission loss at the junction where two terminal ends of the optical fibers or electrical wires are joined together inside the connector.

In medical devices involving optical measurements, such as oximetry devices, connectors are used to functionally connect a sensor probe to a system unit or console which has components such as a display, processor, and other components. Optical fibers or electrical wires in the sensor probe typically run uninterrupted from an oximeter sensor at the distal end of the sensor probe, through a cable, to a connector. The connector physically and functionally connects the sensor probe to a receptacle mounted on the console. The connector axially aligns and connects the ends of optical fibers (or electrical wires) from the sensor probe with their counterparts in the receptacle.

It is important that the connector properly aligns terminal ends of conductors with their counterparts in the receptacle on the console so that signal transmission is optimized. Furthermore, it is desired that the connector of a sensor probe is simple to use. Typically, a sensor probe for an oximetry device is disposed after a single use. Thus, a medical professional needs to attach and detach sensor probes to a console after each use. It is desired that proper connection between a connector of a sensor probe and a receptacle on a console is intuitive and easy for the medical professional so that no inadvertent mistake is made during the connection.

Embodiments of the invention meet this and other needs.

BRIEF SUMMARY OF THE INVENTION

A connector of a sensor probe and its receptacle mounted on a console (which is configured to mate with the connector of the sensor probe) have security mechanisms that ensure proper connection between the connector and the receptacle. The security mechanisms include a hardware feature. For example, a blocking cylinder present in the receptacle prohibits the connector of the sensor probe to be inserted if it is not properly aligned with the receptacle. The security mechanism also includes a software feature where the console prohibits optical measurements by the sensor probe if the connector of the sensor probe is not inserted into the receptacle on the console in a specific orientation.

In one aspect of the invention, the connector of the sensor probe has a housing that includes a first end portion, a second end portion on the opposite side of the first end portion. The housing of the connector also has a first end face at the first end portion and a second end face at the second end portion, where the first and second end faces are generally parallel to each other. The housing of the connector also includes a number of apertures which extend along a longitudinal axis of the connector from the first end face to the second end face. Some of the apertures are filled with conductors, such as optical fibers, electrical wires, or both. Among the apertures, a top portion of one aperture has a diameter larger than other apertures, and it is configured to receive a blocking cylinder head of a receptacle on a console.

In another aspect of the invention, the receptacle on a console includes a distal end portion which is configured to mate with the connector of the sensor probe. The receptacle includes a proximal end portion on the opposite side of a distal end portion, where the proximal end portion is configured to be affixed to a console. The receptacle also includes a distal end face at the distal end portion and a proximal end face at the proximal end portion, where the distal and proximal end faces are generally parallel to each other.

The receptacle also has a number of apertures along a longitudinal axis of the receptacle between the distal end face and the proximal end face, where the apertures are to be aligned with their counterpart apertures in the connector. Some of the apertures are filled with optical fibers, electrical wires, or both. The receptacle also includes a blocking cylinder having a head portion that has a larger diameter than a tail portion of the blocking cylinder. The tail portion of the blocking cylinder is inserted into one aperture, and the head portion of the blocking cylinder protrudes from the aperture at the distal end face.

The head portion of the blocking cylinder is configured to fit into one of apertures in the connector of the sensor probe. If the blocking cylinder is not properly inserted into the cylinder receiving aperture in the connector of the sensor probe, the connector of the sensor probe cannot be properly connected to the receptacle on the console. Furthermore, an identifier circuit in the console will prohibit any optical measurements from the sensor probe when the blocking cylinder head of the receptacle is not fully inserted into an aperture in the connector of the sensor probe.

In yet another aspect of the invention, a sensor probe includes an oximeter sensor comprising a first source structure and a first detector structure, a connector, and a cable that joins the oximeter sensor to the connector. The cable includes conductors (e.g., optical fibers, electrical wires, or both), and distal ends of the conductors are connected to the first source structure and the first detector structure of the oximeter sensor and proximal ends of the conductors are inserted and connected to apertures in the connector.

In yet another aspect of the invention, a tissue retractor sensor probe includes a retractor for retracting a tissue, where the retractor has a shaft, a handle coupled to a proximal end of the shaft, and a tip coupled to a distal end of the shaft. The tip of the tissue retractor sensor probe includes a retractor portion and an oximeter sensor. The tissue retractor sensor probe also includes a cable which connects the oximeter sensor probe to a connector, which is used to functionally connect the tissue retractor sensor probe to its receptacle on the console.

In yet another aspect of the invention, an adapter can convert a conventional receptacle without a blocking cylinder to a new receptacle with a blocking cylinder so that it is configured to receive a connector of a sensor probe in accordance with the present invention. The adapter can include a receptacle member and a connector member which are enclosed in a single housing. Alternatively, the receptacle member and the connector member of the adapter are connected by a cable.

In yet another aspect of the invention, a method includes determining whether there is a conduction path between a blocking cylinder in a receptacle on a console and a metal pin which is inserted in an aperture of a connector of a sensor probe, prior to making any tissue oxygen saturation measurements.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 4A shows a cross-sectional view of a connector of a sensor probe.

FIG. 4B shows a longitudinal sectional view of the connector shown in FIG. 4A when the connector is sliced along a line connecting between two A's.

FIG. 5A shows a cross-sectional view of a receptacle on a console.

FIG. 5B shows a longitudinal sectional view of the receptacle shown in FIG. 5A when the receptacle is sliced along a line connecting between two B's.

FIG. 6B shows a longitudinal sectional view of a connector of a sensor probe with a metal pin and an optical fiber in apertures of the connector.

FIG. 6C shows a cross-sectional view of a receptacle on a console.

FIG. 9A shows a longitudinal sectional view of an adapter that includes a female connector member at one end of the adapter, and a male receptacle member at the opposite end of the connector member.

FIG. 9B shows a longitudinal sectional view of another adapter that includes a female connector member at one end of the adapter, and a male receptacle member at the opposite end of the connector member.

DETAILED DESCRIPTION OF THE INVENTION

In one aspect of the invention, a connector of a sensor probe and its receptacle on a console (which is configured to receive and mate with the connector of the sensor probe) have security mechanisms that ensure proper connection between the connector and the receptacle. In one embodiment, the connector and receptacle have physical security features that block insertion of the connector into the receptacle if they are not aligned in a proper orientation. In another embodiment, the console includes a software security feature that allows optical measurements from the sensor probe only if the connector and receptacle are properly connected.

In another aspect of the invention, an adapter can be used to convert a conventional receptacle on a console into a receptacle with security features in accordance with the present invention. A new receptacle provided by the adapter also makes it easier for the user to align and attach a sensor probe to the console. The new receptacle also minimizes a risk that the user may inadvertently insert the connector of the sensor probe into its receptacle on the console in a wrong orientation, which can potentially damage components in the sensor probe or console.

In yet another aspect of the invention, an adapter can be provided with a cable which lengthens the connection between a console and a sensor probe. The adapter with a cable is useful in situations when a surgical setting requires a patient to be kept at a distance from the console because of potential contamination issues.

The connector and receptacle assemblies can include optical fibers or fiber optic bundles for optical transmission, electrical wires for electrical transmission, or both. In this application, optical fibers, fiber optic bundles, or electrical wires are collectively referred to as conductors.

Examples of embodiments of the invention are illustrated using figures and are described below. The figures described herein are used to illustrate embodiments of the invention, and are not in any way intended to be restrictive of the broad invention. Embodiments of the invention are not limited to the specific arrangements and constructions shown and described. For example, features shown in one figure can be combined with features shown in another figure.

Figure 1:
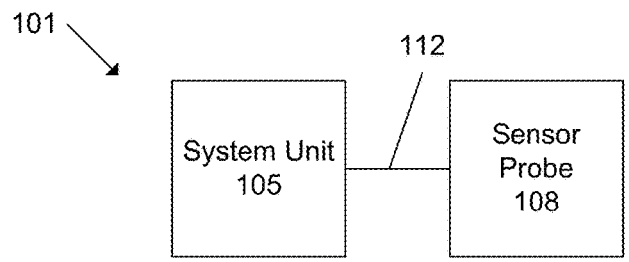
FIG. 1 shows a block diagram of an oximeter system for measuring oxygen saturation of tissue in a patient.

FIG. 1 shows an oximeter system 101 for measuring oxygen saturation of a tissue in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., nerve or skin) at a site where oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142, 7,355,688, and 7,525,647. These patents are assigned to the same assignee as this patent application and are incorporated by reference along with all other references cited in this application.

Figure 2:
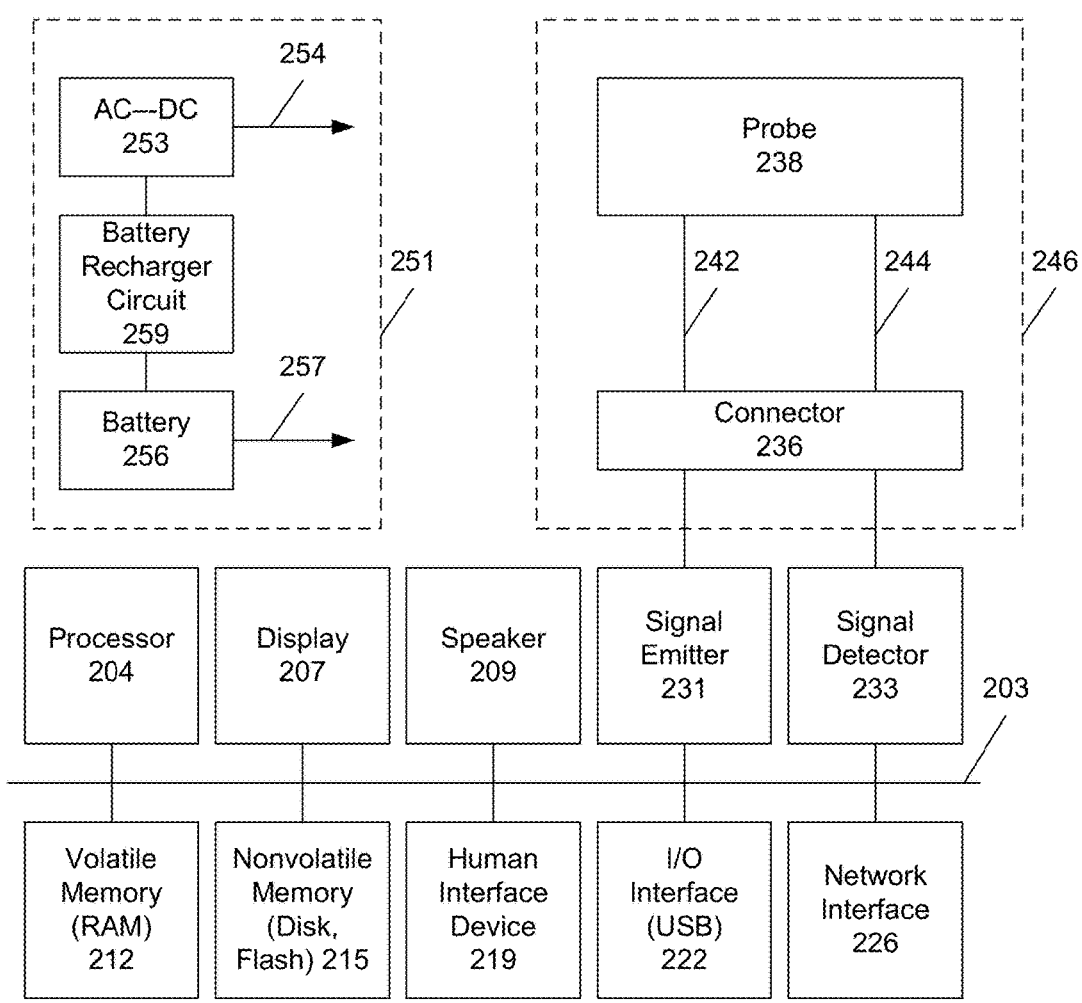
FIG. 2 shows a more detailed block diagram of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

Connector 236 may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects a cerebral probe is connected, the system uses cerebral probe algorithms and operation. When the system detects that a thenar probe is connected, the system uses thenar probe algorithms and operation. When the system detects that a nerve retractor sensor probe is connected, the system uses nerve retractor probe algorithms and operation. A system can handle any number of different types of probes. There may be different probes for measuring different parts of the body, or different sizes or versions of a probe for measuring a part of the body (e.g., three different thenar probe models).

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

Probe 246 may be a handheld tool and a user moves the probe from one point to another to make measurements. However, in some applications, probe 246 is part of an endoscopic instrument or robotic instrument, or both. For example, the probe is moved or operated using a guiding interface, which may or may not include haptic technology.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www-.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
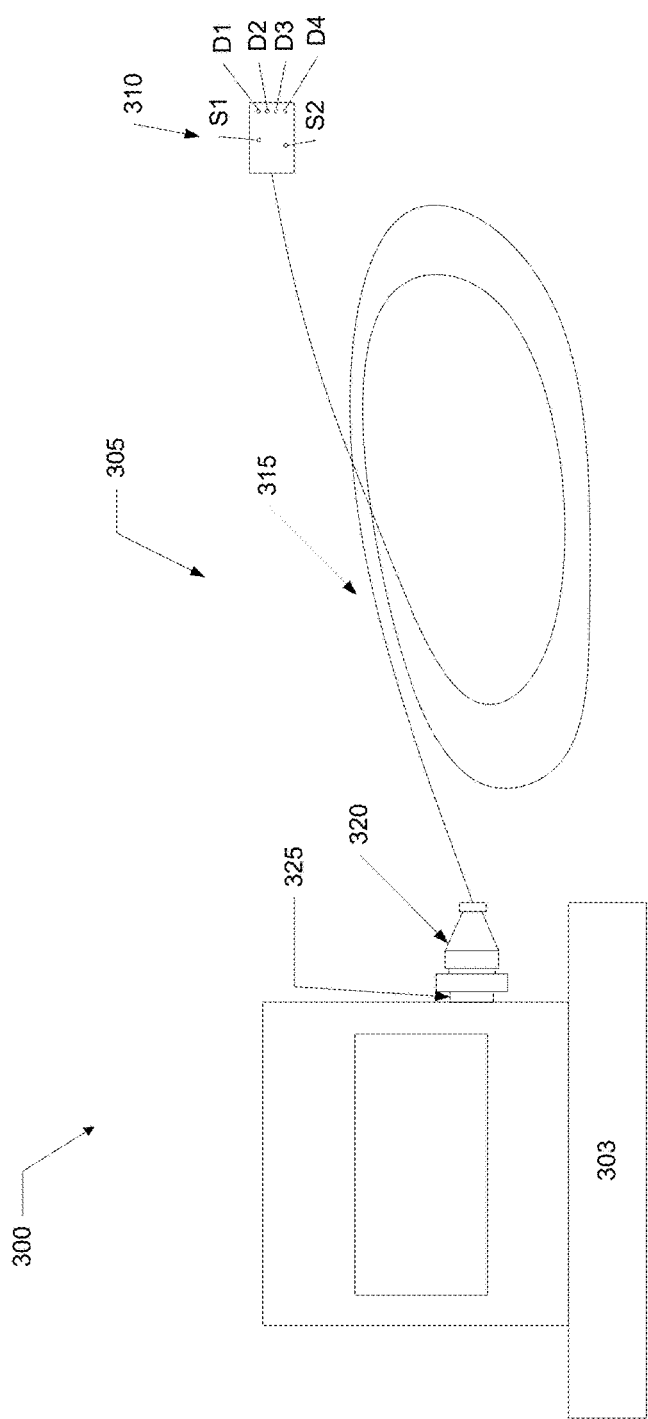
FIG. 3 shows a system of the invention including a monitoring console with a receptacle and a small patch sensor probe, where the small patch sensor probe includes an oximeter sensor, cable, and connector.

FIG. 3 shows one implementation of a system 300 which includes a monitoring console 303 and a sensor probe 305. Sensor probe 305 includes an oximeter sensor or oximeter sensor unit 310, a cable 315, and a connector 320, where one end of the cable is connected to the probe and the other end of the cable is connected to the connector. Connector 320 is removably attached to a receptacle 325 which is affixed to or mounted on the monitoring console. For example, the receptacle can be mounted onto the console housing by a set of screws. The connector and receptacle have security features which assist the user in connecting them together in a correct orientation and in mated condition.

Oximeter sensor unit 310 measures oxygen saturation of a tissue. Each oximeter sensor unit includes at least one source structure and at least one detector structure. A source structure is a structure in the oximeter sensor unit that provides light that can be transmitted into a tissue. The source structure can generate light, or it can be a structural component that transmits light generated elsewhere (e.g., from an upstream source). A detector structure is a structure in the oximeter sensor unit that detects light (or that is a structural component of the detection process) which is scattered and reflected from the tissue.

In the implementation shown in FIG. 3, oximeter sensor unit 310 includes two source structures (S1 and S2) and four detector structures (D1, D2, D3, and D4) on its scanning surface that contacts a target tissue. The source structures and detector structures are shown as openings in oximeter sensor unit 310, and they may be referred to as openings or sensor openings in this application. The source structures and detector structures are physically and functionally connected to console 303 by conductors (e.g., optical fibers, electrical wires, or both) which run from the sensor unit to connector 320 inside the cable. The connector of the sensor probe aligns and couples the conductors with their counterparts in the receptacle of the console.

In one embodiment, a source structure can be a laser or light emitting diode (LED) that emits a light of a specific wavelength suitable to monitor oxygen saturation. A detector structure can be a photodiode (e.g., a PN diode, a PIN diode, or an avalanche diode) that detects the light transmitted and reflected from a tissue, after the source structure emits the light into the tissue. In an oximeter sensor unit, both LEDs and photodiodes are located at the scanning surface of the oximeter sensor unit. These LEDs and photodiodes can then be electrically connected to a system unit or console. In this embodiment, since the light is generated next to the tissue surface and subsequently detected at the tissue surface, there is less attenuation of a signal.

In another embodiment, a source structure is an opening in an oximeter sensor unit (at its scanning surface) with an optical fiber inside, which is connected to an emitter located elsewhere (e.g., system unit). Likewise, a detector structure is an opening in an oximeter sensor unit (at its scanning surface) with an optical fiber inside, which is connected to a detector located elsewhere. The optical fibers from each oximeter sensor unit are then connected to either an emitter or a detector which may be located in a system unit or console.

In the latter embodiment, one or more optical fibers run along the length of the cable, and distal ends of the optical fibers (or fiber optic bundle) is inserted or attached to sensor openings. The proximal ends of the optical fibers terminate inside connector 320. The proximal ends of the optical fibers in the connector are aligned with their corresponding optical fibers in the receptacle of the console, so that light generated in the console can be delivered to the oximeter sensor of a sensor probe.

While FIG. 3 illustrates an embodiment with six sensor openings in the oximeter sensor, any suitable number of sensor openings can be present in the sensor probe. For example, there may be one, two, three, four, five, six, seven, or eight or more sensor openings. Any one or more sensor openings can be source structures, and any one or more sensor openings can be detector structures. A number of source structures can be equal to a number of detector structures in the oximeter sensor unit, or they can be different.

Further, oximeter sensor unit 310 shown in FIG. 3 has a particular sensor opening pattern where the arrangement of source structures and detector structures are asymmetrical. The detector structures are aligned in a linear row and source structures are offset from each other. In other words, a line drawn through the detector structures is not parallel to a line drawn through the source structures. Additionally, the distance between openings D1 and D4 is shorter than the distance between openings S1 and S2.

In a specific implementation, a line drawn through openings D1 and S1 is perpendicular to a line drawn through openings D1 and D4. Also, a line drawn through openings D1 and D4 is perpendicular to a line drawn through openings D4 and S2. Also, a distance between openings D1 and D4 is five millimeters. A distance between each of the openings D1, D2, D3, and D4 is 5/3 millimeters. A distance between D1 and S2 is five millimeters. A diameter of an opening is one millimeter.

The selection of a number of sensor openings and sensor opening pattern for a sensor unit depends on many factors. For example, a small number of sensor openings would require a relatively small scanning surface and thus a small sensor unit can be produced. A large number of sensor openings may increase sensitivity of optical measurements. Furthermore, a larger separation between a source structure and a detector structure may allow the detector structure to detect light after the light has penetrated deeper into the tissue, compare to a sensor unit with a smaller separation between the two structures.

There are various other implementations of sensor opening patterns which can be incorporated into an oximeter sensor unit. Sensor opening patterns can be either symmetrical or asymmetrical. Some of these implementations are discussed in U.S. Pat. No. 7,355,688, U.S. patent application Ser. No. 12/126,860, filed May 24, 2008, and U.S. patent application Ser. No. 12/178,359, filed Jul. 23, 2008. These patent and patent applications are assigned to the same assignee as this patent application and are incorporated by reference. Any of the asymmetrical or symmetrical arrangements of sources and detectors discussed in these patent and patent applications are applicable to the source structures and detector structures in this application.

In one implementation, console 303 (sometimes referred to as a monitoring console or system unit) shown in FIG. 3 can be a portable console which may be hand carried. A portable console can follow a patient and optical measurements can be made anywhere in the hospital. In this implementation, it is desirable that the portable console is battery-operated. In another implementation, the console may be a large, nonportable device that is attached to a wall or secured to a stand. In this implementation, the system is typically connected to AC power.

The console may include a mass storage device to store data. Mass storage devices may include mass disk drives, floppy disks, magnetic disks, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, oxygen saturation measurements and the time and date measured. The oxygen saturation measurements may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

The console also includes a display screen which may display the patient's data, such as an oxygen saturation measurement. The screen may be a flat panel display or include a touch screen interface so that the user can input data into the console.

The console, in addition to the display, may also include a processor, signal emitter circuit, signal detector circuit, and a receptacle to removably couple ends of one or more conductors. In a specific implementation, the ends of one or more conductors (e.g., optical fibers or electrical wires) are instead permanently connected to the console. The signal emitter circuit may operate to send a signal through the one or more conductors. The signal detector circuit then receives a signal via one or more conductors.

In a specific implementation, the signal emitter circuit may include one or more laser emitters, light emitting diode (LED) emitters, or both. The signal emitter circuit may be used to generate an optical signal having two or more different wavelengths to be transmitted through the sensor unit. The wavelengths may range from about 600 nanometers to about 900 nanometers.

In a specific implementation, the console includes a first radiation source and a second radiation source. The radiation sources may be dual wavelength light sources. In other words, first radiation source provides two wavelengths of radiation and second radiation source provides two wavelengths of radiation. First radiation source, second radiation source, or both may include one or more laser diodes or light emitting diodes (LEDs) that produce light in any wavelength, but typically the wavelengths range from about 600 nanometers to about 900 nanometers. In a specific implementation, a first wavelength of light is generated that has a wavelength of about 690 nanometers. A second wavelength of light is generated that has a wavelength of about 830 nanometers.

In a specific implementation, one or more near-infrared radiation sources are included within the console. In other implementations, the radiation sources may be external to the console. For example, the radiation sources may be contained within a separate unit between the console and sensor probe. The radiation sources may, for example, be contained in an oximeter sensor unit itself or in other parts (e.g., in the handle of a tissue retractor sensor probe). In yet another implementation, some radiation sources may be within the console while other radiation sources are external to the console.

These radiation sources may be near-infrared lasers. In a specific implementation, there is one near-infrared laser located within the console. In other implementations, there may be more than one near-infrared laser. For example, there may be 2, 3, 4, 5, 6, 7, 8, 9, 10 or more than 10 radiation sources. In another implementation, the radiation sources may include those that produce a visible light.

In one implementation, light emitted by different radiation sources is provided to a beam combiner via optical fibers. The beam combiner effectively merges the light from different radiation sources, and the merged light is then provided via output optical fibers. The output fibers are arranged to allow the merged or combined light to be homogenized to ensure that the light is substantially uniformly distributed across the output fibers when the light enters the sensor unit. The beam combiner may be located in the console, or may be located outside of the console.

In a specific implementation, a single pulse of light is transmitted into the tissue. In another implementation, multiple pulses of light may be transmitted into the tissue. For example, a first pulse of light may be received by a first detector. A second pulse of light may be received by a second detector.

When light is transmitted to a target tissue via source structures in the sensor unit, light scatters due to heterogeneous structure of the tissue, and some of the light is absorbed by chromophores such as hemoglobin. An attenuated version of the light that is reflected by the tissue is detected by detector structures in the sensor unit and is transmitted to the console. The oxygen saturation or hemoglobin concentration of the tissue can be calculated based on a value of the initial light generated by the signal emitter and a value of an attenuated version of the light that is reflected from the tissue and is subsequently detected by the signal detector.

In a specific implementation, an attenuation ratio is used to determine tissue oxygen saturation ($StO_2$), hemoglobin concentration (Hgb), or both. Additional details on attenuation methods are also discussed in U.S. patent application Ser. No. 12/126,860, filed May 24, 2008, which is incorporated by reference. The attenuation ratio method may also include techniques discussed in U.S. Pat. No. 6,587,701, which is incorporated by reference.

In the automatic error-cancellation or self-calibration scheme, the system factors such as source intensity, detector gain, and loss of light in the optical fibers and connectors are cancelled automatically. The automatic error-cancellation scheme is discussed in more detail as equations 5a and 5b in U.S. Pat. No. 6,597,931, which is incorporated by reference. The self-calibration scheme may also include equations discussed in U.S. Pat. Nos. 6,516,209, 6,735,458, and 6,078,833, U.S. patent application Ser. No. 12/126,860, filed May 24, 2008, and *New Optical Probe Designs for Absolute (Self-Calibrating) NIR Tissue Hemoglobin Measurements*, Proc. SPIE 3597, pages 618-631 (1999), which are incorporated by reference.

In embodiments of the invention, the length of the cable may vary. In a specific implementation, the length of the cable ranges from about 1.2 meters to about 3 meters. For example, the cable may be about 1.3, 1.4, 1.5, 1.6, 1.7, 1.8, 1.9, 2, 2.1, 2.2, 2.3, 2.4, 2.5, 2.6, 2.7, 2.8, 2.9, or 3.0 meters long or greater. Depending on the specific application, the cable length may be less than 1.2 meters. In some applications, the cable length will be greater than 3 meters. It may be desirable to use longer cables when a patient is immune compromised and needs to be kept away from sources of contamination, such as a console.

Connector 320 at the end of the cable attaches the sensor probe to its receptacle on the console. The connector also protects the cable from accidental disconnection. The connector may include a collar that threads onto the receptacle on the console. Alternatively, the connector may include a lug closure, press-fit, or snap-fit components.

In a specific implementation, the console can provide alerts to the user when a proper connection is made between the sensor probe and the console. The alerts may be visual (e.g., a flashing light on a display of console), audible, or both. The display monitor may also show a type of sensor probe (e.g., small patch sensor probe, nerve retractor sensor probe, and others) that is attached to the console, as well as other information.

In a specific implementation, there may be other connectors on the cable besides connector 320 and receptacle 325. These other connectors allow the cable to be separated into two or more pieces, allow additional lengths of cable to be attached, or both.

These additional connectors provide several benefits. For example, the cable attached to the oximeter sensor can be disposed along with the oximeter sensor after use. The cables attached to the console can be reused. Thus, the cable more likely to be contaminated, i.e., the cable attached to the oximeter sensor, can be disposed. The cable less likely to be contaminated, i.e., the cable attached to the console can be reused. As another example, the connectors may be used to attach additional lengths of cable to extend the overall length of the cable.

In an implementation, the cable includes one or more optical wave guides enclosed in a flexible cable jacket. The optical wave guides may be used to transmit light from the console, through the oximeter sensor and out openings in the oximeter sensor and into the tissue. The optical wave guides may also be used to transmit the light received from the tissue back to the console.

The optical wave guides may have the shape of a polygon, such as a square, rectangle, triangle, or other shape. In other cases, the optical wave guides may have circular or oval shapes. In a specific implementation, the optical wave guides are multiple strands of fiber optic cable. The flexible cable jacket may be thin-walled PVC with or without an aluminum helical monocoil, shrink wrap tubing, plastic, rubber, or vinyl.

In a specific embodiment, all of the fiber optic cables are enclosed within one end, or both ends of the flexible cable jacket. Minimizing the number of exposed cables lowers the likelihood that the cables will get entangled. In another embodiment, the fiber optic cables are not enclosed together and instead each fiber optic cable is enclosed in its own flexible cable jacket.

In a specific implementation, the cable is passive. For example, it will not contain any active, generative properties to maintain signal integrity. However, in other implementations, the cable may include active components. The cable may include active components to amplify the signal transmitted through the sensor unit, received at the sensor unit, or both. For example, long lengths of cable subject to significant attenuation may require amplification. Amplification may also be required if the monitored site contains a particularly dense structure such as bone. In a specific implementation, radiation sources such as light emitting diodes (LEDs) may be placed in the sensor unit. Thus, the cable may contain electrical wiring to transmit power to the radiation sources.

In an embodiment of the invention, each opening on the sensor unit and corresponding cable is dedicated to a particular purpose. For example, a first opening on the sensor unit (and corresponding fiber optic cable) is dedicated to transmitting light from the monitoring console. A second opening on the sensor unit is dedicated to transmitting a signal received at the second opening to the monitoring console.

Some embodiments use a particular opening and cable for multiple purposes (e.g., both input and output) using a scheme such as multiplexing.

In a specific embodiment, a particular opening and cable transmits an output to affect a reaction (e.g., sending electrical signals to stimulate muscle or other tissue). Another opening and cable transmits the resultant signal back to the monitoring device. In yet another embodiment, the openings and cables may simply detect changes and transmit these changes back to the monitoring device. For example, the openings and cables may carry voltage changes in the patient's skin back to the monitoring device.

In an implementation, the connectors on the cable, monitoring console, probe, and combinations of these have indicators. The indicators may be color indicators that are painted on, or raised indicators, or both. These indicators help the user to properly attach the cable to the monitoring console, probe, or both. For example, the indicators may include green arrows placed on the cable connectors, monitoring console, and probe. Alignment of the arrows indicates proper attachment of the cables. Further, there may be instructions printed on the console, cable, and probe oximeter that instruct the user on the proper attachment of the cable.

FIG. 4A illustrates a cross-sectional view of one embodiment of a connector 400 of a sensor probe when the connector is viewed from the console side. In other words, FIG. 4A is a view that the user will see when the user looks into an end face of the connector. FIG. 4B shows a longitudinal sectional view of the connector shown in FIG. 4A.

FIG. 5A shows a cross-sectional view of a receptacle 500 on a console which is configured to receive the connector shown in FIG. 4A. The receptacle view shown in FIG. 5A is a view that the user will see when the user looks into the receptacle from outside of the console. FIG. 5B shows a longitudinal sectional view of the receptacle shown in FIG. 5A.

As shown in FIG. 4A, the connector of a sensor probe has a housing 455 that has fourteen apertures (numbered 1 through 14) which are generally parallel to one another and extend along the longitudinal axis of the housing. The apertures are arranged in four rows—a first row having three apertures; a second row having four apertures that are offset from the apertures of the first row; a third row having four apertures that are aligned with the apertures of the second row; and a fourth row having three apertures that are offset from the apertures of the third row but are aligned with the apertures of the first row.

Among the fourteen apertures shown in FIG. 4A, aperture number 2, 3, 7, 11, 13, and 14 are filled with conductors (e.g., optical fibers or electrical wires). Other aperture can be empty, or may include features that serve special functions, such as assisting in alignment of the connector with the receptacle on the console. For example, aperture numbers 6 and 9 represented by double concentric circles have metal pins which assist the console to determine what type of sensor probe is attached to the console, which will be described more in detail below along with FIGS. 6A through 6C.

FIG. 4B shows a longitudinal sectional view of connector 400 when the connector is sliced along a line connecting two A's, across aperture numbers 4 through 7 shown in FIG. 4A. As shown in FIG. 4B, the housing has an internal cavity 463 at a first end portion 460 of the housing, and a first end face 461 which is recessed inside the internal cavity. There are also four passageways or apertures (numbers 4, 5, 6, and 7), where aperture number 7 is filled with a conductor 442. As shown in FIG. 4B, a terminal end of conductor 442 may protrude from the first end face.

The connector further includes a collar 457 which is slidably mounted onto an outer surface of the housing of the connector. The remaining portion of the collar can be separated from the housing of the connector, providing a groove 458 between the housing and the collar. An end portion of the receptacle can be inserted into groove 458 of the connector, and the collar can assist securing the connector to the receptacle mounted on the console. The collar can have multiple ridges 459 around its outer surface to assist the user to have a better grip around the collar when it is secured onto the receptacle.

FIG. 5A shows a cross-sectional view of one embodiment of a receptacle 500 which is configured to receive the connector of the sensor probe shown in FIG. 4A. The receptacle is typically affixed, attached, or mounted on a housing of the console. The receptacle contains terminal ends of conductors (e.g., optical fibers, electrical wires, or both) which are configured to align and couple with their counterparts in the connector of a sensor probe. The conductors have first terminal ends in the receptacle and their second terminal ends are connected to various components in the console (e.g., photodetector, radiation sources, and others).

In FIG. 5A, the receptacle has a core member 510 which is surrounded by a sleeve member 520. The core member and the sleeve member are separated by a concentric channel 525. When the connector on the sensor probe and the receptacle on the console are brought together, housing 455 of the connector is inserted into channel 525 of the receptacle, and sleeve member 520 of the receptacle is inserted into groove 458 of the connector.

As shown in FIG. 5A, the receptacle also has fourteen apertures which are to be aligned with apertures of the connector shown in FIG. 5A, when the connector and receptacle mate together. The fourteen apertures of the receptacle will align with their respective apertures in the connector. For example, aperture number 1 of the receptacle will align with aperture number 1 of the connector; aperture number 2 of the receptacle will align with aperture number 2 of the receptacle, and so forth. The corresponding pairs of apertures of the connector and receptacle are shown as a mirror image of each other in FIGS. 4A and 5A.

In one implementation, a proximal end of a conductor 442 (e.g., optical fiber) may extend beyond the first end face of the connector housing as shown in FIG. 4B. The protruded conductor is received by its counterpart aperture in a receptacle of a console. As shown in FIG. 5B, a terminal end of a conductor 542 in the receptacle is not flushed against the end surface. Instead, the terminal end of conductor 542 is receded inside the aperture, providing a gap for conductor 442 from the connector to enter into the aperture of the receptacle. By having conductors of the connector insert themselves into the apertures of the receptacle of the console, light or signal transmission loss can be further minimized.

While the connector shown in FIG. 4A and the receptacle shown in FIG. 5A have fourteen apertures, they can include any suitable number of apertures. For example, the connector and receptacle may include 10, 20, 30, 40, 50, or any other number of apertures between these numbers.

The connector and the receptacle shown in FIGS. 4A through 5B have several security features that ensure that they are connected in one or specific orientations. The security features include both a hardware mechanism (e.g., a physical block) and a software mechanism.

In one implementation, the connector and receptacle assembly has physical security features that block insertion of the connector into the receptacle if they are not aligned in a proper orientation. As shown in FIGS. 5A and 5B, the receptacle has a blocking cylinder 531 in aperture number 4. The blocking cylinder has a shape of a stepped cylinder where its head or top portion has a diameter larger than a bottom or tail portion of the cylinder. The tail portion of the cylinder fits into the aperture of the receptacle, whereas the head or top portion of the blocking cylinder (referred to as "blocking cylinder head") sits above the end face, outside of the aperture.

The blocking cylinder on the receptacle can be made of any suitable material, as long as it does not interfere with signal transmission. For example, the blocking cylinder may be made of a metal, plastic, ceramic, composite material, and others.

For the connector of the sensor probe shown in FIG. 4B, a top portion of aperture number 4 near the internal cavity has a diameter larger than the remaining portion of aperture number 4 or other apertures. The top portion of aperture number 4 is configured to receive blocking cylinder head 531 of the receptacle. This aperture is referred to as a "cylinder receiving aperture" in this application. The user can align and insert the blocking cylinder head of the receptacle into the cylinder receiving aperture (aperture number 4) of the connector. Because of a difference in aperture size, the user can readily recognize and align the cylinder receiving aperture in the connector with the blocking cylinder head of the receptacle on the console.

The blocking cylinder head of the receptacle and the top portion of the cylinder receiving aperture of the connector have specific shapes and sizes so that the blocking cylinder head fits only into the top portion of the cylinder receiving aperture of the connector, but not into any other apertures.

For example, the blocking cylinder head of the receptacle may have a diameter of about 4.5 millimeters, whereas the top portion of the cylinder receiving aperture of the connector has a diameter slightly larger than 4.5 millimeters, such as between about 4.6 millimeters to about 5.5 millimeters, more typically about 5.0 millimeters. Other apertures in the connector (and also in the receptacle) and the remaining portion of the cylinder receiving aperture can have a diameter between about 2.0 millimeters to 4.0 millimeters, more typically about 3.0 millimeters, so that the blocking cylinder head cannot be inserted into these apertures.

The dimensions described above for the apertures and the blocking cylinder head are merely exemplary, and they can have any suitable dimensions as long as the top portion of the cylinder receiving aperture of the connector have a larger diameter to receive the blocking cylinder head of the receptacle, and other apertures in the connector have a diameter too small to receive the blocking cylinder head. For example, other apertures (and also a bottom portion of the cylinder receiving aperture) in the connector can have a diameter which is between about 50 to 80 percent, more typically about 60 percent, smaller than a diameter of a top portion of the cylinder receiving aperture.

The blocking cylinder head of the receptacle can also vary. For example, the blocking cylinder head can have a diameter of between about 4.0 millimeters to 5.0 millimeters, whereas the cylinder receiving aperture of the connector can have a diameter slightly larger than the selected diameter of the blocking cylinder head.

Further, the blocking cylinder head may have a length between about 1 millimeter to about 3 millimeters, whereas the tail portion of the blocking cylinder can have a length ranging between about 5 millimeter to about 15 millimeters. In a specific implementation, the head portion of the blocking cylinder has a length of about 2 millimeters, where as the tail portion of the blocking cylinder has a length of about 10 millimeters.

The top portion of the cylinder receiving aperture has a depth that has the same dimension or deeper than the length of the blocking cylinder. For example, if the blocking cylinder head has a length of 2 millimeters, then the top portion of the cylinder receiving aperture has a depth of about 3 millimeters. In a specific implementation, the top portion of the cylinder receiving aperture has a depth of about 2 millimeters to about 5 millimeters.

While FIG. 4B shows that only the top portion of the cylinder receiving aperture has a larger diameter than other apertures, in some implementation, the entire length of the cylinder receiving aperture may have a diameter larger than other apertures. Further, although the blocking cylinder and cylinder receiving aperture are located in aperture number 4 of the receptacle and connector, respectively, they can be located at any other suitable apertures in the receptacle.

Further, although the use of a single blocking cylinder in a receptacle is illustrated, more than one blocking cylinder can be used in embodiments of the invention. For example, a receptacle may include two, three, four, or more blocking cylinders in different apertures, and a connector may include a corresponding number of cylinder receiving apertures.

In a specific implementation, the blocking cylinder in the receptacle and the cylinder receiving aperture on the connector may be color coded to further assist the user. For example, the blocking cylinder on the receptacle and the cylinder receiving aperture can be color matched (e.g., red, yellow, orange, green, and others) so that the user can readily identify the two elements, and insert the blocking cylinder head of the receptacle into the colored aperture of the connector.

In another implementation, the connector and receptacle have additional physical security features that allow them to be connected in single or specific orientations. For example, housing 455 of the connector has multiple keying nubs 456 which protrude from the outer surface of the housing and which run longitudinally along the length of the housing. The multiple keying nubs on the housing may differ in size or may be unevenly spaced from one another.

An interior surface of the sleeve member of the receptacle has recessed regions 537 which are shaped so that they can receive keying nubs 456 of the connector. Since each keying nub of the connector and its complementary recessed region in the receptacle have unique shapes, typically one particular keying nub will fit into one particular recessed region. Thus, the keying nubs of the connector and their corresponding recessed regions in the receptacle assist the user in joining the connector and the receptacle in a proper orientation.

In yet another implementation, the connector of the sensor probe and its receptacle can have additional features which prevent accidental disconnection of the connector from the receptacle. In one embodiment, the collar of the connector can have helical threads around its inner surface and can act as a female screw member. The collar can radially rotate about a threaded end portion of the receptacle to secure the connector of the sensor probe onto its receptacle on the console.

In another embodiment, the collar can have one or more latch elements 447 (shown in FIG. 4A) molded integrally with collar in its inner surface for engaging latch recesses or slots on the receptacle (not shown in FIG. 5A). These and other features can prevent the user from accidentally disconnecting the connector of the sensor probe from the receptacle.

In yet another implementation, the console can include a software security feature that allows optical measurements from the sensor probe only if the connector and the receptacle are properly connected. For example, the console can include an identifier circuit which can determine whether or not the blocking cylinder head of the receptacle is properly inserted into the cylinder receiving aperture of the connector of the sensor probe. The identifier circuit can communicate with other components in the console (e.g., signal emitter circuit) to initiate measurements of tissue oxygen saturation once it determines that a proper connection is made between the connector and the receptacle.

Figure 5C:
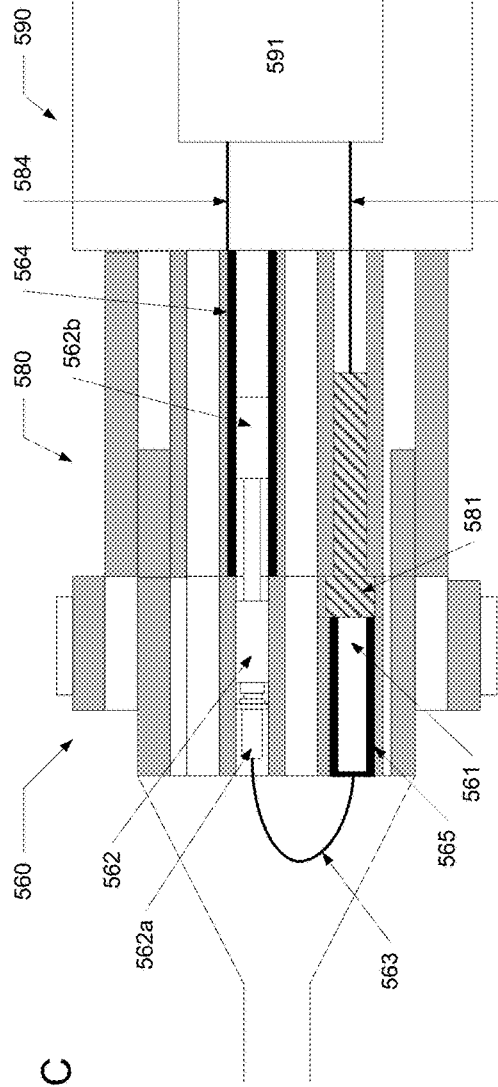
FIG. 5C shows a longitudinal sectional view of a connector of a sensor probe which is fully inserted and connected to its receptacle on a console.

FIG. 5C illustrates an example where a connector 560 of a sensor probe is properly connected to its receptacle 580 on a console 590. A blocking cylinder head 581 is fully inserted into a cylinder receiving aperture 561 of the connector. A metal pin 562 which is also inserted in another aperture of the connector. A terminal end 562b of the metal pin is inserted into a corresponding aperture in the receptacle. A terminal end 562a of the metal pin and the blocking cylinder are electrically connected by a wire loop 563. The cylinder receiving aperture includes a metallic sleeve 565 which provides an electrical contact between the blocking cylinder head and the wire loop. Thus, the blocking cylinder and the metal pin are electrically connected on the connector side.

The blocking cylinder and the metal pin are also electrically connected on the receptacle side. A tail portion of the blocking cylinder is electrically connected to an identifier circuit 591 by a conductor 583. The terminal end of the metal pin is surrounded by a metallic sleeve 564. The metallic sleeve is connected to the identifier circuit by a conductor 584, thereby providing an electrical connection between the metal pin and the identifier circuit.

As shown in FIG. 5C, when the blocking cylinder head of the receptacle is fully inserted into the cylinder receiving aperture of the connector, there is a closed circuit among the identifier circuit, blocking cylinder, and metal pin. The identifier circuit can transmit a signal through either conductor 583 or conductor 584 to determine if there is a closed circuit.

In one implementation, wire loop 563 can be a low resistance metallic wire. In this implementation, the identifier circuit senses a short circuit conduction between the metal pin and the blocking cylinder. The identifier circuit can subsequently send a signal to a processor in the console to apply suitable algorithms to initiate tissue oxygen saturation measurements.

In another implementation, wire loop 563 can include a resistor having a specific resistance value (e.g., 10-100 kiloohms). In this implementation, the identifier circuit can send a signal and determine whether there is a conduction path between the blocking cylinder and the metal pin with a specified resistance value. Once the identifier circuit determines that there is a conduction path with a specified resistance value, the identifier circuit can transmit a signal to the processor in the console to apply suitable algorithms to initiate oxygen saturation measurements.

Figure 5D:
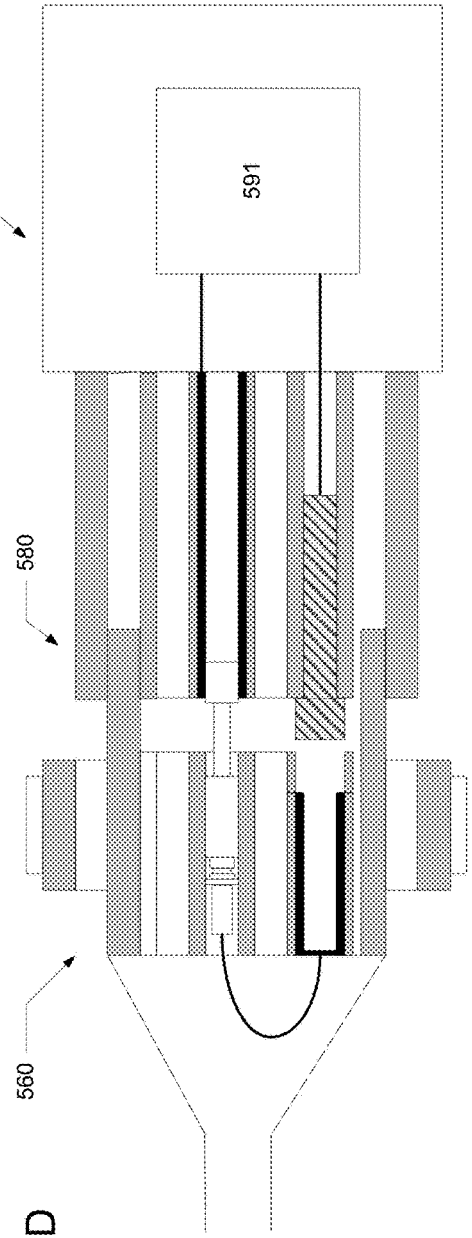
FIG. 5D shows a longitudinal sectional view of a connector of a sensor probe which is incompletely inserted and improperly connected to its receptacle on a console.

FIG. 5D shows the same connector and receptor assembly as shown in FIG. 5C, but they are not completely connected to each other. There may be a situation where the user inadvertently does not fully insert a connector of a sensor probe into its receptacle on the console. As shown in FIG. 5D, the blocking cylinder head of the receptacle has not been inserted into the blocking cylinder receiving aperture of the connector. Thus, there is no conduction path between the blocking cylinder and the metal pin.

When the identifier circuit sends a signal through either conductor 583 or 584 in FIG. 5D, the identifier circuit will determine that there is an open circuit. The identifier circuit can then send a signal to the processor in the console to prohibit any initiation of tissue oxygen saturation measurements. The identifier circuit can further send a signal to a display or speaker to alert the user that the connector of the sensor probe and its receptacle on the console are not properly connected.

Thus, by using both hardware features (e.g., a physical block by a blocking cylinder) and software features, the system not only provides an easy way to align the connector of the sensor probe and its receptacle on the console, the system also provides a safeguard against making optical measurements when the sensor probe is not properly connected to the console.

Figure 6A:
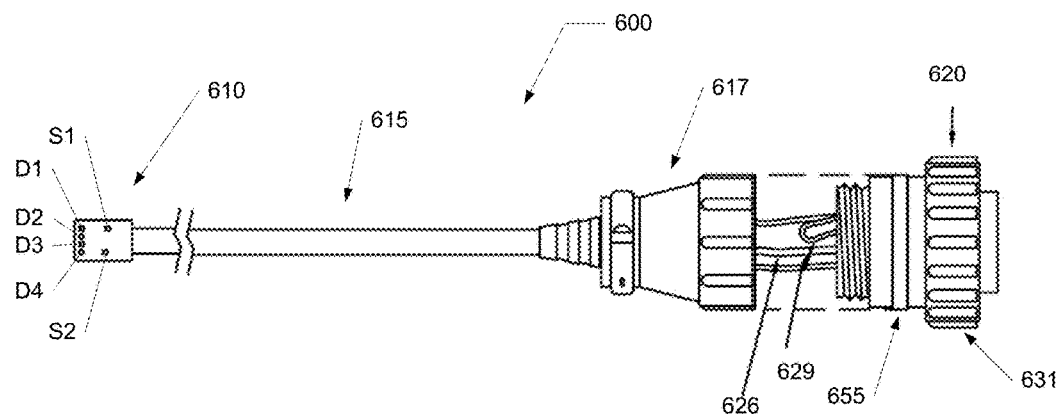
FIG. 6A shows a sensor probe where a connector at its distal end is separated from the rest of the sensor probe to show internal components of the sensor probe.
Figure 6A:
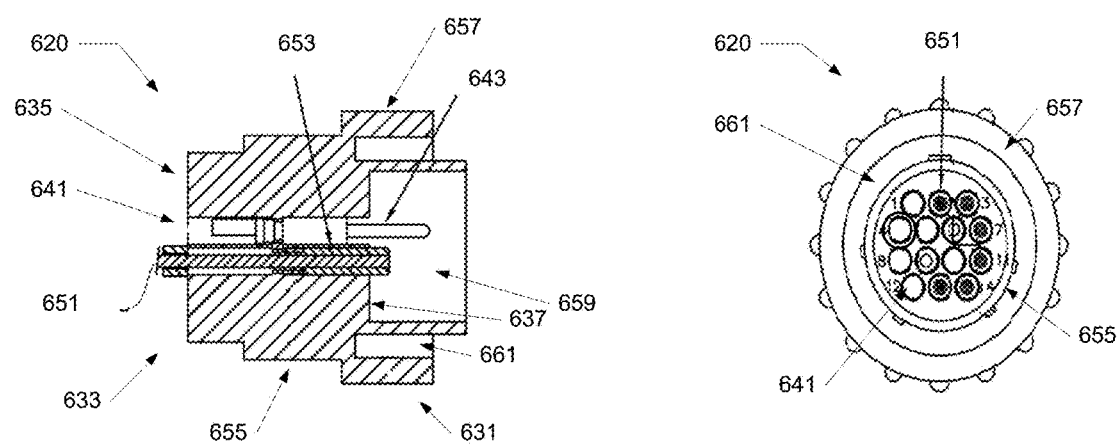

In another aspect of the invention, FIG. 6A shows one implementation of a sensor probe 600, where the sensor probe has a feature that allows the console to automatically determine which type of sensor probe is connected to the receptacle on the console. There are different types of sensor probes (e.g., a nerve retractor sensor probe, small patch sensor probe, surgical elevator sensor probe, and others), and they use different algorithms to measure tissue oxygen saturations. While the system may provide a user interface (e.g., keyboard, touchpad screen, voice activated input, and others) and the user can manually input information, it may be desirable to have a system which automatically recognizes a type of sensor probe that is inserted into the receptacle on the console.

As shown in FIG. 6A, sensor probe 600 includes an oximeter sensor 610, a cable 615 which is connected to the oximeter sensor at one end and to a cable end member 617 at the other end. The sensor probe also includes a connector 620 which is connected to the cable end member. The cable end member is configured so that it allows the cable to be joined to connector 620. For example, the cable end member has threads in its inner surface so that it can be threaded onto one end of the connector. The opposite end of the connector can then be removably attached to a receptacle affixed to a console (not shown in FIG. 6A).

The connector has a housing 655 which contains optical fibers and other components. The connector also has a collar 631 which assists in securing the connector of the sensor probe onto the receptacle mounted on the console.

As shown in FIG. 6A, cable end member 617 and connector 620 are disconnected from each other so that components inside the sensor probe can be shown. There are optical fibers 626 which run continuously from the oximeter sensor down to the connector through the cable. The connector also includes a wire loop 629 which connects two metal pins that are inserted in apertures in the connector (not shown in FIG. 6A). As described below, the metal pins with a wire loop connection can be used by the console to distinguish which type of sensor probe is attached to the console.

FIG. 6B shows a longitudinal sectional view of connector 620 shown in FIG. 6A. The connector includes a housing 655 which holds optical fibers and other components. The housing of the connector includes a first end portion 631, a second end portion 633, a first end face 637 at the first end portion, and a second end face 635 at the second end portion. First end face 637 is positioned inside an internal cavity 659 at the first end portion of the housing. There are a number of apertures 641 which extend from the first end surface to the second end surface of the housing of the connector.

The connector also includes a collar 657 which is attached to the housing at one end and can rotate about the housing and joins the connector to the receptacle of the console. A groove 661 between the housing and the collar of the connector provides space to receive a sleeve member of a receptacle. The collar can be engaged onto a male counterpart of the receptacle to provide a tight seal between the sensor probe and the receptacle mounted on the console.

As shown in FIG. 6B, some of the apertures may be filled with optical fibers 651. The optical fibers are typically protected by the use of spring ferrules 653 in the connector. A ferrule is a component (typically a rigid tube) used to align and protect a stripped end of an optical fiber. A ferrule is used together with a connector that connects the optical fiber to another optical fiber or to a device. The ferrules keep the optical fibers accurately aligned within the connector. Ferrules can be made of glass, plastic, metal, or ceramic material. The use of spring ferrule in the connector reduces loss of light when light passes through the interface between the optical fiber in the connector and the optical fiber in the receptacle of the console.

In one implementation, apertures in the connector may include metal pins 643 as shown in FIG. 6B. Typically, two or more metal pins are inserted into apertures in the housing of the connector. The metal pins are electrically connected by wire loop 629 at the second end portion of the connector as shown in FIG. 6A. The metal pins provide means for the console to automatically distinguish which type of sensor probe is connected to the console, without any input from the user.

FIG. 6C shows a cross section of connector 620, viewed from the first end portion of the housing of the connector. The cross section of the connector shows a collar 657 and a housing 655. Inside the housing, there are fourteen apertures 641. Six out of fourteen apertures, aperture numbers 2, 3, 7, 11, 13, and 14, are filled with glass fiber bundles that lead to probe sensor openings S2, S1, D1, D3, D2, and D4, respectively.

Typically, the number of optical fibers or glass fiber bundles present in the connector depends on the number of sensor openings that are present in the oximeter sensor unit. In some applications, a probe may have one, two, three, four, five, six, seven, eight, or more sensor openings, and corresponding number of optical fibers. Some of the apertures in the connector may remain empty and unused (e.g., aperture number 1, 5, 8, 10, and 12) as shown in FIG. 6C.

In one implementation, the connector includes a feature that allows the console to determine which sensor probe is connected to the console. For example, different sensor probes can be designed to have different electrical properties at the connector. As shown in FIG. 6C, a sensor probe of FIG. 6A can have aperture numbers 6 and 9 in the connector filled with metal pins (represented by a double circle) which are electrically connected by a wire loop at the second end portion of the connector housing.

When the connector of the sensor probe is properly inserted into its receptacle on the console, an identifier circuit in the console receives a voltage or other signal from metal pins located at aperture numbers 6 and 9. The wire loop connecting these two metal pins provides a short circuit or other form of conductive path between these two metal pins. The identifier circuit senses this short-circuit condition between the metal pins located in aperture numbers 6 and 9. The identifier circuit can subsequently send a signal to a processor in the console. Based on the aperture numbers that are involved in a short circuit, the processor can determine which type of sensor probe is attached to the console. Then, the processor applies suitable algorithms and steps to make optical measurements from the sensor probe.

In one implementation, the identifier circuit shown in FIGS. 5C and 5D can also be used to determine which type of sensor probe is attached to the console. Furthermore, one of the two metal pins in the connector used to identify a type of sensor probe can be used to provide a conduction path for the blocking cylinder. For example, the metal pin in aperture number 9 shown in FIG. 6C can be used to identify that a small patch oximeter sensor unit is attached to the console (along with the metal pin in aperture number 6). The same metal pin in aperture number 9 can be metal pin 562 shown in FIG. 5C which provides a conduction path for the blocking cylinder. Thus, one of the metal pins in the connector can serve a dual purpose.

When a different sensor probe is attached to the connector (e.g., a nerve retractor sensor probe with two optical fibers), metal pins can occupy different apertures in the connector. For example, for a nerve retractor sensor probe, the metal pins can be inserted into aperture numbers 9 and 10. When the identifier circuit in the console determines that there is a short circuit condition between aperture numbers 9 and 10, then it can send a signal to a processor that a nerve retractor sensor probe is attached to the console. By inserting the metal pins into different sets of apertures in the connector, the console can automatically determine which sensor probe is connected to the console.

In embodiments of the invention, the connector and receptacle can be made of any suitable materials. For example, the housing and collar of the connector and the core member and sleeve member of the receptacle can be molded of plastic material (e.g., dielectric thermoplastic material).

Furthermore, the connector and other components shown in FIGS. 6A through 6C can have any suitable dimensions. In a specific implementation, when the cable end member and connector are tightly screwed together, they may have a combined length of about 80 millimeters. Also, the diameter of the connector (including the collar) shown in FIG. 6C can be about 33 millimeters, and the diameter of the housing of the connector can be about 20 millimeters.

While the connector and receptacle shown in FIGS. 4A, 5A, and 6C have oval or elliptical cross sections, the connector and receptacle can have any suitable shape. For example, they can have a circular cross section, rectangular cross section, square cross section, octagonal cross sections, and others.

FIGS. 7A, 7B, 8A, and 8B show variations of the connector and receptacle shown in FIGS. 4A through 5B, where both the connector and receptacle have circular cross sections.

Figure 7A:
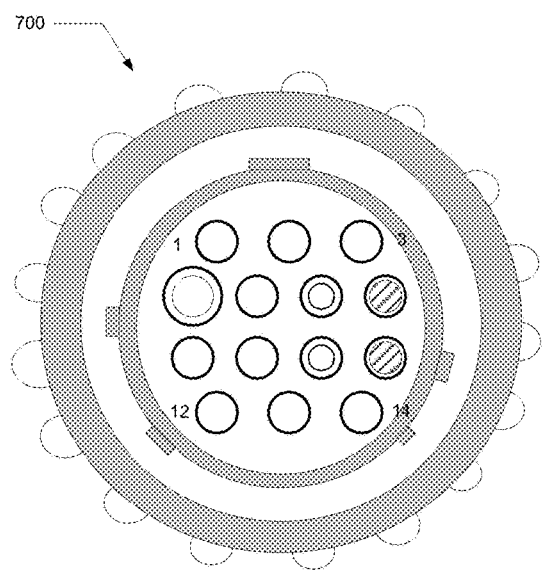
FIG. 7A shows a cross-sectional view of another implementation of a connector of a sensor probe, where two apertures of the connector are filled with conductors.

FIG. 7A shows a cross-sectional view of a connector 700 of another sensor probe. In the embodiment shown in FIG. 7A, two apertures (aperture numbers 7 and 11) of the connector are filled with optical fibers, rather than six apertures as shown in FIG. 4A. The connector shown in FIG. 7A is typically used with a sensor probe with two sensor openings in it oximeter sensor unit.

Figure 7B:
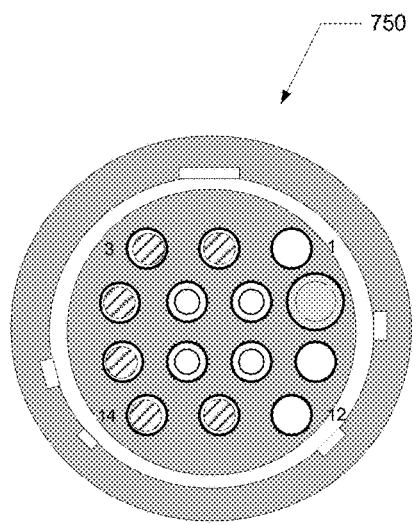
FIG. 7B shows a cross-sectional view of a receptacle which receives the connector shown in FIG. 7A.

FIG. 7B shows a cross-sectional view of a receptacle 750 which is configured to mate with connector 700 of the sensor probe shown in FIG. 7A. Receptacle 750 has six optical fibers in aperture numbers 2, 3, 7, 11, 13, and 14. The receptacle generally contains either the same or higher number of optical fibers compared to the connector. Since the connector has only two optical fibers in aperture numbers 7 and 11, the only optical fibers that will be used in the receptacle are optical fibers in aperture numbers 7 and 11. Other optical fibers in the receptacle (in aperture numbers 2, 3, 13, and 14) are not be utilized since there are no corresponding optical fibers in the connector.

For each type of sensor probe, a connector has metal pins occupying different apertures in the connector. For example, in FIG. 7A, the connector has metal pins occupying aperture numbers 6 and 10 (represented by double circles). The metal pins are electrically connected by a wire loop as shown in FIG. 6A. When an identifier circuit in the console sends an electrical signal to each aperture in the receptacle and determines that there is a short circuit condition between aperture numbers 6 and 10, then the identifier circuit can send a signal to a processor, identifying a type of sensor probe that is attached to the receptacle.

Figure 8A:
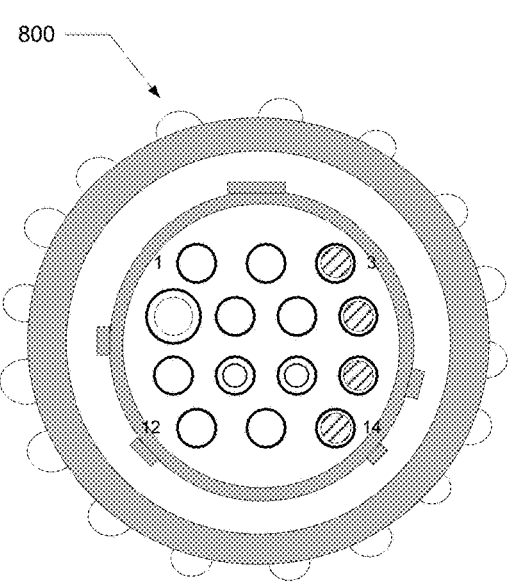
FIG. 8A shows a cross-sectional view of yet another implementation of a connector of a sensor probe, where four apertures of the connector are filled with conductors.

FIG. 8A shows a cross-sectional view of a connector 800 of another sensor probe. In the embodiment shown in FIG. 8A, four apertures (aperture numbers 3, 7, 11, and 14) of the connector are filled with optical fibers, rather than two apertures as shown in FIG. 7A. The connector shown in FIG. 8A is typically used with a sensor probe with four sensor openings in its oximeter sensor unit.

Figure 8B:
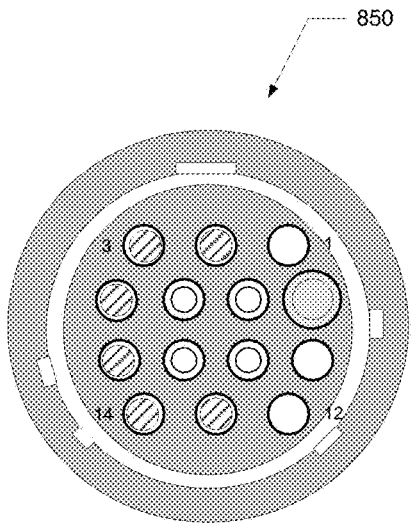
FIG. 8B shows a cross-sectional view of a receptacle which receives the connector shown in FIG. 8A.

FIG. 8B shows a cross-sectional view of a receptacle 850 which is configured to mate with connector 800 of a sensor probe shown in FIG. 8A. The receptacles shown in FIGS. 7B and 8B are identical. Typically, a single receptacle is attached or affixed to the console, and the same receptacle is used for inserting a number of different sensor probes. Thus, the receptacle may have the same or higher number of optical fibers than connectors of sensor probes. Depending on the number of optical fibers present in the connector, there may be extra optical fibers in the receptacle that do not have complementary optical fibers in the connector.

In another aspect, embodiments of the invention include an adapter which can be used to convert a conventional receptacle (i.e., without a blocking cylinder) which is affixed to a console into a receptacle with a new design (i.e., with a blocking cylinder).

FIG. 9A illustrates a longitudinal sectional view of an adapter 900 that includes a female connector member 901 at one end of the adapter, and a male receptacle member 903 at the opposite end of the connector member. The female connector member of the adapter can be attached to the conventional receptacle which is affixed to the console. Then, the male receptacle member of the adapter can be used to connect a sensor probe with a connector in accordance with the present invention.

Female connector member 901 of the adapter has substantially same elements as a connector of a sensor probe shown in FIG. 4B. For example, the female connector member has a housing 920 with multiple apertures 921 that run along the longitudinal axis of the housing. In FIG. 9A, one of the apertures has an optical fiber 907. The female connector member also has a collar 925 around the housing. The collar assists in stably connecting and securing the connector of a sensor probe to the receptacle mounted on the console.

Male receptacle member 903 of the adapter also has substantially same elements as the receptacle shown in FIG. 5B. The male receptacle member has multiple apertures 931. One or more apertures can be filled optical fibers 907. The male receptacle member also has a blocking cylinder which is inserted into one of the apertures. The blocking cylinder has appropriate dimensions so it can fit into a cylinder receiving aperture in the connector of a sensor probe.

In one implementation, the female connector member and the male receptacle member of the adapter can be functionally connected together by a cable 905 as shown in FIG. 9A. The cable can have one or more optical fibers which run uninterruptedly from apertures of a receptacle member to apertures of a connector member of the adapter. For example, optical fiber 907 has one terminal end in receptacle member 903 and the other terminal end in connector member 901.

In another implementation, a connector member and a receptacle member of an adapter can be adjoined together in a single housing enclosure, rather than being connected by a cable. For example, cable 905 shown in FIG. 9A can be omitted, and a proximal end 913 of the receptacle member can be adjoined to and integral with a proximal end 915 of the connector member of the adapter to form an adapter in a single housing enclosure. It may be desirable to use an adapter in a single housing rather than an adapter with a cable, if it is not necessary to extend the overall length of a sensor probe.

FIG. 9B illustrates a longitudinal sectional view of another adapter 950 that includes a female connector member 951 at one end of the adapter, and a male receptacle member 903 at the opposite end of the connector member.

The female connector member of the adapter can be attached to a receptacle on the console which has features shown in FIGS. 5A and 5B. The male receptacle member of the adapter can be connected a connector of a sensor probe shown in FIGS. 4A and 4B. The adapter shown in FIG. 9B can be used to extend the overall length of a cable between a console and an oximeter sensor.

The elements shown in FIG. 9B are substantially same as the elements shown in FIG. 9A, except for an aperture 961 in the female connector member of the adapter. Aperture 961 has a top portion which has a larger diameter than the rest of the aperture or other apertures. Aperture 961 is configured to receive a blocking cylinder head on a receptacle mounted on a console.

In one implementation, the female connector member and the male receptacle member of adapter 950 can be functionally connected together by a cable. In another implementation, a connector member and a receptacle member of an adapter can be adjoined together in a single housing, rather than being connected by a cable, if it is not necessary to extend the overall length of a sensor probe.

While the connector and receptacle are shown to be used with a sensor probe with a small patch oximeter sensor unit shown in FIGS. 3 and 6A, the connectors and receptacles in accordance with the present invention can be used to connect any type of sensor probes to a console. For example, a sensor probe can be a cerebral sensor probe which measures oxygen saturation of brain tissue. Details of a cerebral sensor probe are discussed in U.S. patent application Ser. No. 12/116,013 filed May 6, 2008, which is incorporated by reference.

In another example, a sensor probe can be a spot probe or pen probe which measures oxygen saturation of a small tissue area. A spot probe or pen probe is shown and discussed in FIG. 14 of U.S. patent application Ser. No. 12/178,359 filed Jul. 23, 2008, which is incorporated by reference.

In yet another example, a sensor probe can be a thenar sensor probe which measures oxygen saturation of thenar area in the thumb. Details of a thenar sensor probe are discussed in U.S. patent application Ser. No. 12/110,994 filed Apr. 28, 2008, which is incorporated by reference.

In some embodiments, the connector and receptacle in accordance with the present invention can be used with sensor probes that have an additional function other than measuring oxygen saturation of a tissue. For example, a sensor probe can be a surgical elevator sensor probe which can elevate and manipulate a tissue and measure oxygen saturation of the tissue. Details of a surgical elevator sensor probe are discussed in U.S. patent application Ser. No. 12/194,508 filed May 19, 2008, which is incorporated by reference.

Figure 10:
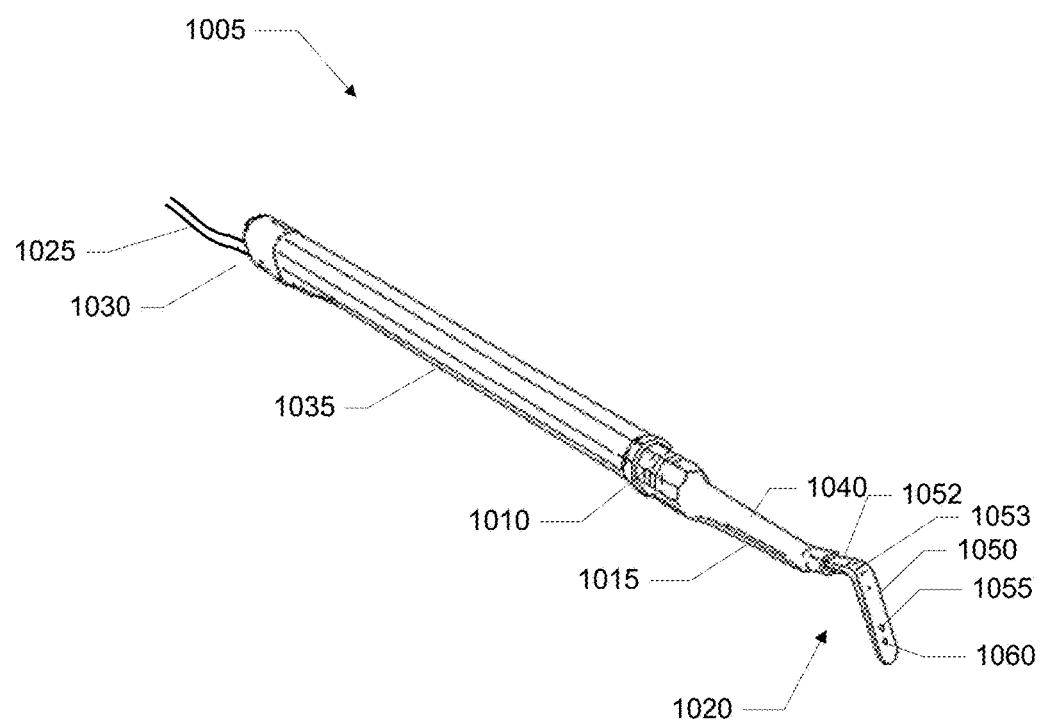
FIG. 10 shows a surgical elevator sensor probe.

An example of a surgical elevator sensor probe is shown in FIG. 10. A surgical elevator has an oximeter sensor at its tip, which allows measuring of oxygen saturation of a tissue. Surgical elevators play an important role in medicine. Depending on the surgical procedure, elevators may be used to measure, elevate, manipulate, or cut. One area of medicine in which surgical elevators are typically used is during spinal surgery.

FIG. 10 shows a perspective view of a surgical elevator 1005. The surgical elevator includes a handle 1010, connected to a shaft 1015, connected to a tip 1020. A cable 1025 exits at a proximal end 1030 of the handle. The handle may be at least partially enclosed by a handle jacket 1035. The shaft may be at least partially enclosed by a shaft jacket 1040. The tip includes a first blade portion 1050 that is connected to a second blade portion 1052 at a connection 1053. In a specific embodiment, the first blade portion includes two openings including openings 1055 and 1060 which function as an oximeter sensor.

Another example of a sensor probe that has a dual function is a tissue retractor sensor probe. A tissue retractor sensor probe can retract a tissue, such as a nerve, in addition to measuring oxygen saturation of the tissue at the point of contact. Details of a tissue retractor sensor probe are discussed in U.S. patent application Ser. No. 12/126,860, filed May 24, 2008, which is incorporated by reference.

Figure 11:
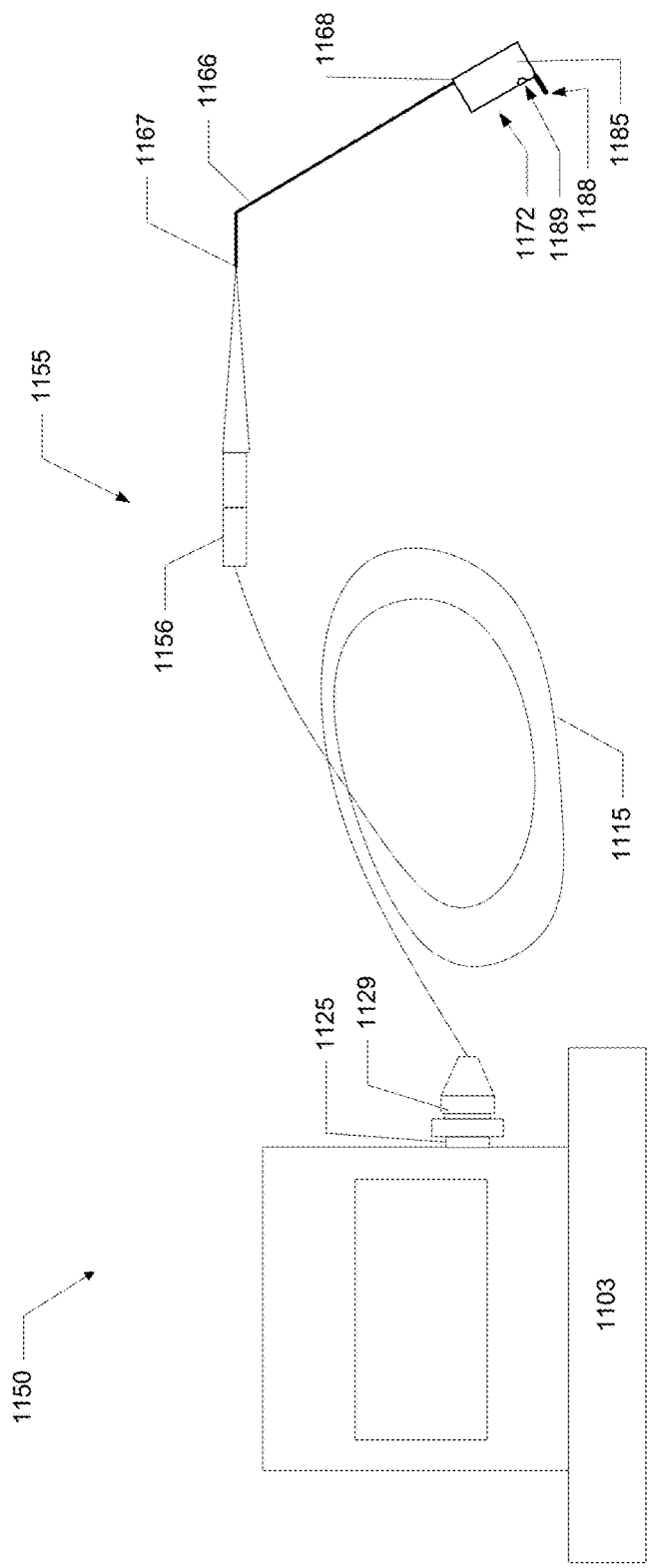
FIG. 11 shows an implementation of a system which includes a monitoring console with a receptacle and a nerve retractor sensor probe with a connector.

FIG. 11 shows an implementation of a system 1150 which includes a monitoring console 1103 and a nerve retractor sensor probe 1155. In this implementation, the nerve retractor sensor probe which has an additional function (i.e., retracting a nerve) in addition to measuring oxygen saturation of the nerve at the point of contact.

As shown in FIG. 11, a nerve retractor sensor probe 1155 includes a retractor that has a handle 1156, a shaft 1166 connected at its proximal end 1167 to the first handle, and a tip 1172 connected to a distal end 1168 of the shaft. The shaft can be made of steel. The tip includes a retractor portion or retractor blade 1188 and an oximeter sensor 1185. Oximeter sensor 1185 has one or more sensor openings 1189 on a bottom surface of the oximeter sensor, adjacent to retractor blade 1188.

The shaft can include an internal channel or passageway. Optical fibers can pass from sensor openings on the tip, through the channel, through the handle, and into a cable jacket or cable insulation. Alternatively, the fibers can be run along the shaft and secured by, for example, shrink wrap. The optical fibers that travel inside or along the shaft are exposed through sensor opening 1189 on a bottom surface of tip 1172. Cable 1115 that includes optical fibers, and terminal ends of the optical fibers are inside connector 1120. The connector aligns termini of these optical fibers with termini of optical fibers present in receptacle 1125 which is attached to system unit or console 1103.

Figure 12:
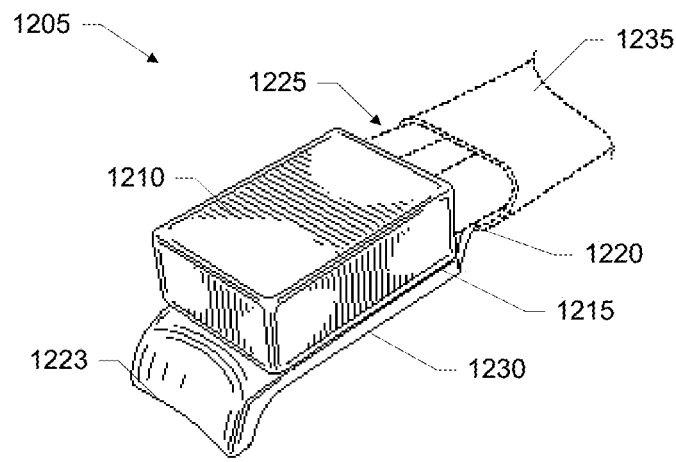
FIG. 12 shows a perspective view of a first implementation of a tip of a nerve retractor sensor probe.

FIG. 12 shows a perspective view of a first implementation of a tip 1205. The tip includes a retractor blade and an oximeter sensor 1210 attached to a top surface 1215 of the tip. The tip attaches to a shaft 1220. The tip also includes a retractor portion 1223. Optical fibers are encased in a cable jacket 1225, travel along the shaft, into the oximeter sensor, and are exposed through an opening on a bottom surface 1230 of the tip. Cable jacket 1225 and shaft are wrapped with a tubing 1235. Such tubing may be heat-shrink tubing.

In a specific implementation of FIG. 12, the tip of the retractor has a length of about 17.5 millimeters, width of about 8 millimeters, and a thickness (not including the retractor blade) of about 5 millimeters.

Figure 13:
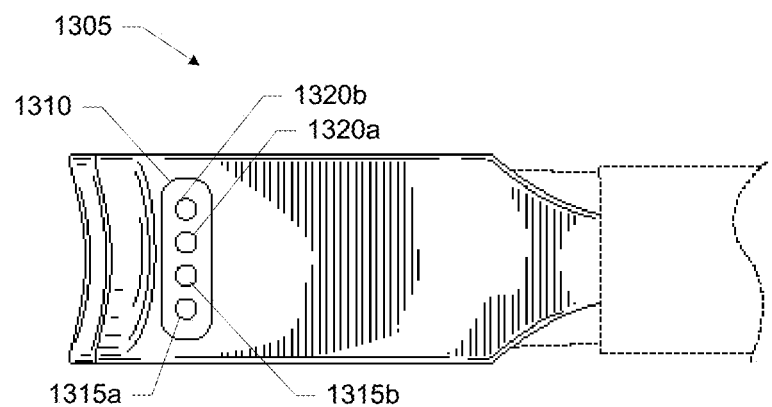
FIG. 13 shows a bottom view of the first implementation of a tip of a nerve retractor sensor probe.

FIG. 13 shows a bottom view of the first implementation of a tip 1305. The tip has a retractor blade and slot 1310, within which there are sensor openings. There are four sensor openings for ends of fiber optic cables. The openings 1315a, 1315b, 1320a, and 1320b are for source and detector fibers.

Since the tip shown in FIG. 13 has four optical fibers, the connector shown in FIG. 8A can be used. As described above, the connector shown in FIG. 8A provides four conductors (e.g., optical fibers) inside four apertures of the connector. These conductors are aligned with the conductors shown in FIG. 8B.

Figure 14:
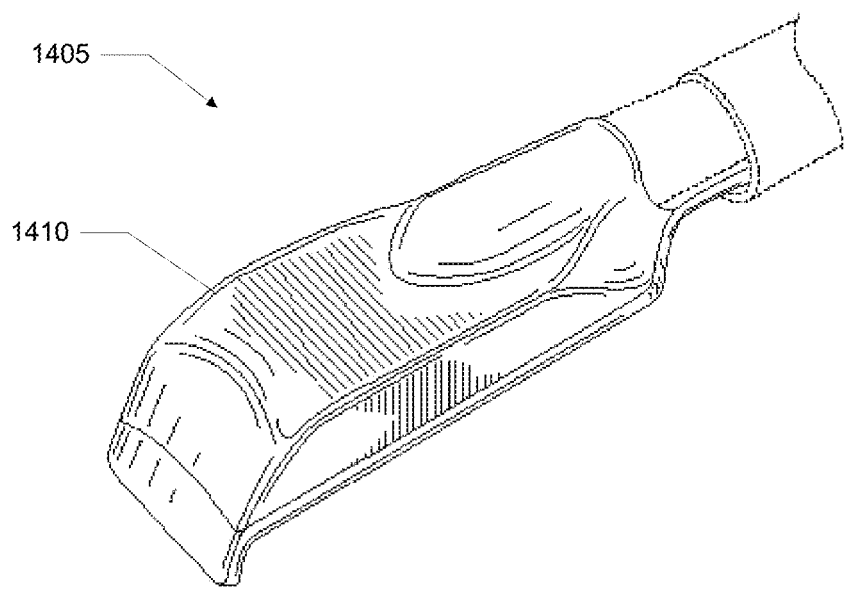
FIG. 14 shows a perspective view of a second implementation of a tip of a nerve retractor sensor probe.

FIG. 14 shows a perspective view of a second implementation of a tip 1405 with an encasement 1410 which contains optical fiber attached to the tip.

In a specific implementation of FIG. 14, the tip of the retractor has a length of about 17.5 millimeters, width of about 8 millimeters, and a thickness (not including the retractor blade) of about 3 millimeters.

Figure 15:
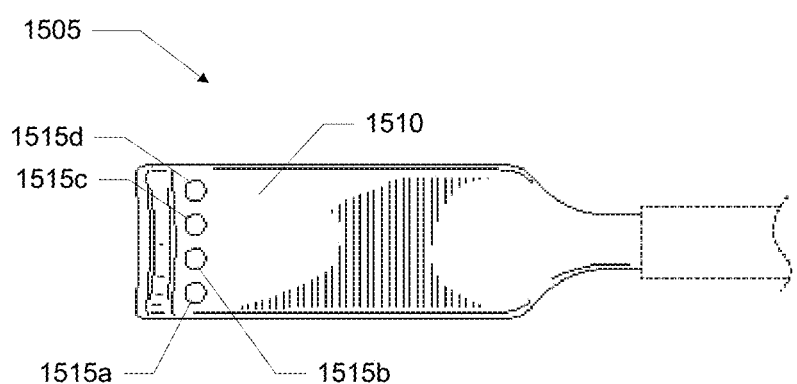
FIG. 15 shows a bottom view of the second implementation of a tip of a nerve retractor sensor probe.

FIG. 15 shows a bottom view of the second implementation of a tip 1505. The tip includes a retractor blade and four sensor openings on a bottom surface 1510 of the tip. The sensor openings include openings 1515a, 1515b, 1515c, and 1515d. Optical fiber is connected to each of the sensor openings. The sensor openings can include sources and detectors.

Figure 16:
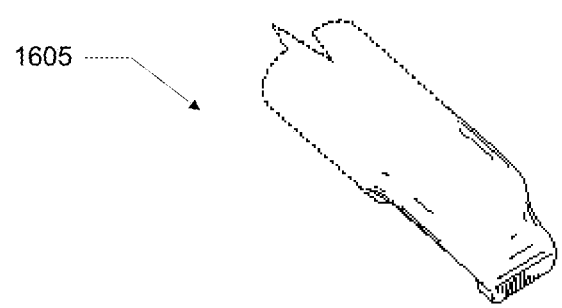
FIG. 16 shows a perspective view of a third implementation of a tip of a nerve retractor sensor probe.

FIG. 16 shows a perspective view of a third implementation of a tip 1605.

Figure 17:
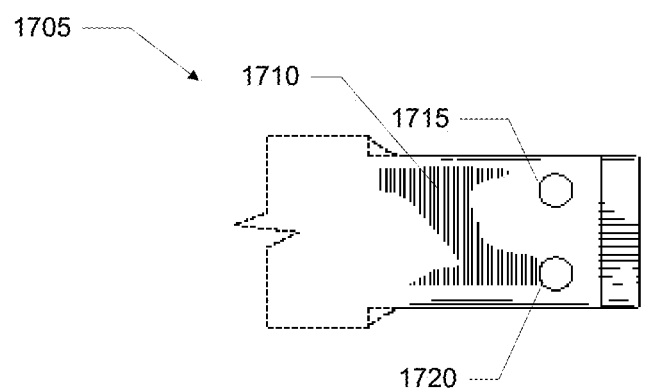
FIG. 17 shows a bottom view of the third implementation of a tip of a nerve retractor sensor probe.

FIG. 17 shows a bottom view of the third implementation of a tip 1705. The tip includes two sensor openings on a bottom surface 1710 of the tip. The two sensor openings include an opening 1715 and an opening 1720. The openings include a source and detector.

Since the tip shown in FIG. 17 has two optical fibers, the connector shown in FIG. 7A can be used. As described above, the connector shown in FIG. 7A provides two conductors (e.g., optical fibers) inside four apertures of the connector. These conductors are aligned with the conductors shown in FIG. 7B.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
providing a first conductor comprising first and second ends and a second conductor comprising third and fourth ends; and
providing a sensor probe comprising:
a handle, comprising an axis, wherein the first and second conductors extend along an axis of the handle; and
a blade, coupled to the handle, comprising a first blade portion and a second blade portion,
wherein the second blade portion is between the first blade portion and the handle,
the first blade portion is angled by a first angle in a first rotation direction relative to the handle's axis and the second blade portion is angled by a second angle in a second rotation direction relative to the first blade portion, where the second rotation direction is opposite of the first rotation direction,
the first blade portion comprises a first side and a second side, the second side of the first blade portion comprises a first sensor structure and a second sensor structure, which will be placed against tissue to be measured,
the first end of the first conductor is coupled to the first sensor structure,
the third end of the second conductor is coupled to the second sensor structure, and
the first side of the first blade portion faces toward the handle, and the second side of the first blade portion faces away from the handle.

2. The method of claim 1 wherein the first conductor is an optical fiber, and the second conductor is an optical fiber.

3. The method of claim 1 wherein a thickness between the first side and second side of the blade is tapered, decreasing in thickness from a proximal end of the blade to the distal end of the blade.

4. The method of claim 1 comprising:
providing a connector, coupled to the second end of the first conductor and fourth end of the second conductor, wherein the connector comprises:
a first end portion;
a second end portion, opposite the first end portion;
a first end face, at the first end portion;
a second end face, at the second end portion; and
a plurality of apertures, extending along a longitudinal axis of the connector from the first end face to the second end face,
wherein at least a first portion of a first aperture of the plurality of apertures comprises a diameter larger than other apertures of the plurality of apertures.

5. The method of claim 4 wherein the first aperture comprises a second portion, the second portion being coupled to the first portion, and second portion comprises the same diameter as at least one other aperture of the plurality of apertures.

6. The method of claim 4 wherein the first conductor is contained within one of the apertures, and a third conductor comprises an electrical conductor, wherein one of the apertures not containing an optical conductor comprises the third conductor.

7. The method of claim 4 wherein the first portion of the first aperture is configured to receive a blocking cylinder head of a receptacle mounted on a console.

8. The method of claim 4 wherein the first portion of the first aperture extends a first distance from the first end face, and the first distance is less than an entire length of the first aperture.

9. The method of claim 4 comprising:
providing a third conductor that is an electrical conductor, wherein one of the apertures not containing an optical conductor comprises the third conductor.

10. A method comprising:
providing a first conductor having a first distal end and a first proximal end;
providing a second conductor having a second distal end and a second proximal end; and
the first and second conductors are coupled to a sensor probe comprising:
a handle, comprising an axis, wherein the first and the second distal ends of the first and the second conductors extend through the handle; and
a blade, coupled to the handle, comprising a first blade portion and a second blade portion,
wherein the second blade portion is between the first blade portion and the handle,
the first blade portion is angled by a first angle in a first rotation direction relative to the handle's axis,
the second blade portion is angled by a second angle in a second rotation direction relative to the first blade portion, where the second rotation direction is opposite of the first rotation direction,
the first blade portion comprises a first side and a second side, the second side of the first blade portion comprises a first sensor structure and a second sensor structure, where the first and second sensor structures will face tissue to be measured,
the first conductor is coupled to the first sensor structure, and the second conductor is coupled to the second sensor structure.

11. The method of claim 10 wherein ends of the first and second conductors terminate at the first and second sensor structures.

12. The method of claim 10 comprising:
providing a connector, coupled to the first and second conductors, wherein the first and second conductors terminate at the connector.

13. The method of claim 10 wherein the first side of the first blade portion faces toward the handle, and the second side of the first blade portion faces away from the handle.

14. The method of claim 10 wherein the first and second conductors comprise optical fibers.

15. The method of claim 10 wherein the first sensor structure is used to emit light into tissue to be measured, and the second sensor structure is used to receive light that is in response to the light emitted from the first sensor structure.

16. The method of claim 10 wherein the sensor probe is a tissue oximeter.

17. The method of claim 10 wherein the first sensor structure is used to emit light having a wavelength in a range from about 600 nanometers to about 900 nanometers.

18. The method of claim 10 comprising:
from the first sensor structure, emitting light into the tissue to be measured;
at the second sensor structure, receiving light from the tissue that is in response to the emitted light from the first sensor structure; and
based on the emitted light and received light, determining an oxygen saturation for the tissue.

19. The method of claim 18 comprising:
providing a visual indication of the determined oxygen saturation on a display.

20. A method comprising:
providing a first conductor having a first distal end and a first proximal end;
providing a second conductor having a second distal end and a second proximal end; and
the first and second conductors are coupled to a sensor probe comprising:
a handle, comprising an axis, wherein the first and the second distal ends of the first and the second conductors extend through the handle; and
a blade, coupled to the handle, comprising a first blade portion and a second blade portion,
wherein the second blade portion is between the first blade portion and the handle,
the first blade portion is angled by a first angle in a first rotation direction relative to the handle's axis,
a first side of the first blade portion faces toward the handle, and a second side of the first blade portion faces away from the handle,
the first blade portion comprises the first side and the second side, the second side of the first blade portion comprises a first sensor structure and a second sensor structure, where the first and second sensor structures will face tissue to be measured,
the first conductor coupled is to the first sensor structure, and
the second conductor is coupled to the second sensor structure.

21. The method of claim 20 wherein ends of the first and second conductors terminate at the first and second sensor structures.

22. The method of claim 20 comprising:
providing a connector, coupled to the first and second conductors, wherein the first and second conductors terminate at the connector.

23. The method of claim 20 wherein the first and second conductors comprise optical fibers.

24. The method of claim 20 wherein the first sensor structure is used to emit light into tissue to be measured, and the second sensor structure is used to receive light that is in response to the light emitted from the first sensor structure.

25. The method of claim 20 wherein the sensor probe is a tissue oximeter.

26. The method of claim 20 wherein the first sensor structure is used to emit light having a wavelength in a range from about 600 nanometers to about 900 nanometers.

27. The method of claim 20 comprising:
from the first sensor structure, emitting light into the tissue to be measured;
at the second sensor structure, receiving light from the tissue that is in response to the emitted light from the first sensor structure; and
based on the emitted light and received light, determining an oxygen saturation for the tissue.

28. The method of claim 27 comprising:
providing a visual indication of the determined oxygen saturation on a display.

* * * * *